(12) United States Patent
Wang et al.

(10) Patent No.: US 9,742,042 B2
(45) Date of Patent: Aug. 22, 2017

(54) VOLTAGE PROTECTION AND HEALTH MONITORING OF BATTERIES WITH REFERENCE ELECTRODES

(71) Applicant: HRL Laboratories, LLC, Malibu, CA (US)

(72) Inventors: Shuoqin Wang, Westlake Village, CA (US); John Wang, Los Angeles, CA (US); Jason A. Graetz, Los Angeles, CA (US); Souren Soukiazian, Agoura, CA (US); Elena Sherman, Culver City, CA (US); Ping Liu, Irvine, CA (US); Mark Verbrugge, Troy, MI (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 14/551,003

(22) Filed: Nov. 22, 2014

(65) Prior Publication Data

US 2015/0147614 A1    May 28, 2015

Related U.S. Application Data

(60) Provisional application No. 61/908,095, filed on Nov. 23, 2013.

(51) Int. Cl.
*H01M 10/48* (2006.01)
*H01M 10/42* (2006.01)
(Continued)

(52) U.S. Cl.
CPC .... *H01M 10/4285* (2013.01); *G01N 27/4161* (2013.01); *G01R 31/362* (2013.01);
(Continued)

(58) Field of Classification Search
CPC ............. H01M 10/4221; H01M 10/48; H01M 10/4285; G01N 27/4161; G01R 31/3606
See application file for complete search history.

(56) References Cited

U.S. PATENT DOCUMENTS 5,633,801 A    5/1997   Bottman
6,339,334 B1   1/2002   Park
(Continued)

OTHER PUBLICATIONS

Xiao et al., "A universal state-of-charge algorithm for batteries," 47th IEEE Design Automation Conference, Anaheim, CA, 2010.
(Continued)

*Primary Examiner* — Jonathan Jelsma
(74) *Attorney, Agent, or Firm* — O'Connor & Company

(57) ABSTRACT

In some variations, an apparatus provides real-time monitoring of voltage and differential voltage of both anode and cathode in a battery configured with at least one reference electrode. Voltage monitors are connected to a computer programmed for receiving anode voltage signals; receiving cathode voltage signals; calculating the derivative of the anode voltage with respect to time or with respect to capacity; and calculating the derivative of the cathode voltage with respect to time or with respect to capacity. Other variations provide an apparatus for real-time assessment of capacities of both anode and cathode in a battery, comprising a computer programmed for receiving electrode voltage signals; estimating first and second electrode open-circuit voltages at two different times, and correlating the first and second electrode open-circuit voltages to first and second electrode states of charge, respectively, for each of anode and cathode. The anode and cathode capacities may then be estimated independently.

27 Claims, 11 Drawing Sheets

(51) Int. Cl.
*G01R 31/36* (2006.01)
*G01N 27/416* (2006.01)
*H01M 10/052* (2010.01)

(52) U.S. Cl.
CPC ..... *G01R 31/3606* (2013.01); *G01R 31/3624* (2013.01); *G01R 31/3679* (2013.01); *H01M 10/4221* (2013.01); *H01M 10/48* (2013.01); *H01M 10/052* (2013.01)

(56) References Cited

U.S. PATENT DOCUMENTS

| | | | |
|---|---|---|---|
| 7,015,701 | B2 | 3/2006 | Wiegand |
| 7,504,835 | B2 | 3/2009 | Byington et al. |
| 8,084,996 | B2 | 12/2011 | Zhang et al. |
| 8,163,410 | B2 | 4/2012 | Fulop et al. |
| 8,268,148 | B2 | 9/2012 | Kirchev et al. |
| 2009/0104510 | A1* | 4/2009 | Fulop ............... H01M 2/30 429/50 |
| 2010/0196758 | A1* | 8/2010 | Hojo ................ H01M 4/60 429/207 |
| 2011/0250478 | A1 | 10/2011 | Timmons |
| 2012/0105068 | A1* | 5/2012 | Wang ............ H01M 10/0525 324/427 |
| 2012/0176092 | A1* | 7/2012 | Fujii ................ G01R 31/361 320/134 |
| 2013/0009604 | A1 | 1/2013 | Bhardwaj et al. |
| 2013/0323542 | A1* | 12/2013 | Wijayawardhana .... H01M 4/00 429/50 |
| 2015/0111077 | A1* | 4/2015 | Paik ................ H01M 2/0285 429/91 |

OTHER PUBLICATIONS

Wang et al., "Multi-parameter battery state estimator based on the adaptive and direct solution of the governing differential equations" Journal of Power Sources 196 (2011) 8735-8741.

Kiani, "Online Detection of Faulty Battery Cells in Energy Storage Systems via Impulse Response Method" 978-1-61284-247-9/11 2011 IEEE.

Zhou and Notten, "Development of reliable lithium microreference electrodes for long-term in situ studies of lithium-based battery systems," J. Electrochem. Soc. 151(12) (2004) A2173-A2179.

U.S. Appl. No. 13/646,663, filed Oct. 6, 2012, for "Methods and Apparatus for Dynamic Characterization of Electrochemical Systems" by Wang et al.

U.S. Appl. No. 13/923,354, filed Jun. 20, 2013, for "Battery With Reference Electrode for Voltage Monitoring" by Wang et al.

U.S. Appl. No. 14/512,128, filed Oct. 10, 2014, for "Methods and Apparatus for Real-Time Characterization of Batteries With a Reference Electrode" by Wang et al.

* cited by examiner

VOLTAGE PROTECTION AND HEALTH MONITORING OF BATTERIES WITH REFERENCE ELECTRODES

PRIORITY DATA

This patent application is a non-provisional application with priority to U.S. Provisional Patent App. No. 61/908,095, filed Nov. 23, 2013, which is hereby incorporated by reference herein.

FIELD OF THE INVENTION

The present invention generally relates to systems and methods to monitor the health and capacity of metal-ion batteries configured with a reference electrode.

BACKGROUND OF THE INVENTION

An electrochemical system is a system that either derives electrical energy from chemical reactions, or facilitates chemical reactions through the introduction of electrical energy. An electrochemical system generally includes a cathode, an anode, and an electrolyte, and is typically complex with multiple scales from nanometers to meters. Examples of these systems include batteries and fuel cells. On-line characterization of batteries or fuel cells in vehicles is difficult, due to very rough noisy environments.

On-line characterization of such electrochemical systems is desirable in many applications, which include real-time evaluation of in-flight batteries on a satellite or aviation vehicle, and dynamic diagnostics of traction batteries for electric and hybrid-electric vehicles. In many battery-powered systems, the efficiency of batteries can be greatly enhanced by intelligent management of the electrochemical energy storage system. Management is only possible with proper diagnosis of the battery states.

In many battery-powered systems such as electric vehicles and satellites, real-time characterization of battery thermodynamic potential and kinetics is desirable. The characterization is crucial for battery states estimation including the state of charge (SOC), the charge and the discharge power capabilities (state of power, SOP), and the battery state of health (SOH).

Current systems typically rely exclusively on voltage monitoring of the full battery cell, which is useful for identifying a problem but is often incapable of preventing damage because the system is triggered during/after the system has exceeded its threshold values. In these systems, the only way to completely avoid damage is to establish conservative threshold values (tighten the operating limits), which limits the performance of the battery.

A three-electrode battery structure (i.e., a battery structure that includes a reference electrode) has one more reference electrode than a conventional battery configuration, which has only two electrodes (cathode and anode). Due to this additional electrode, more current and voltage information is measurable than in conventional batteries. Therefore, a three-electrode configuration is very useful for diagnostics.

Typical in-lab experiments on three-electrode batteries are conducted around equilibrium states; therefore, the measured anode (or cathode) potential against the reference electrode is the open-circuit potential (OCV), also called thermodynamic potential, of the anode (or cathode). However, so far there hasn't been a reliable instrumentation and method to characterize each individual electrode of the battery when the battery is cycling away from equilibrium states, under a random driving profile. In many applications, such as electric vehicles, batteries are usually driven in high rates and therefore are not around equilibrium.

Methods, systems, and apparatus are sought which are capable of characterizing each individual electrode of a three-electrode battery, including open-circuit potentials, when the battery is cycling in a non-equilibrium state and under a random driving profile. What is desired is a simple, direct method of monitoring the voltage and differential voltage of each electrode independently in a battery. In a typical battery, the management system relies only on the voltage from the full cell. However, the full cell voltage is a poor indicator of the health of each electrode.

SUMMARY OF THE INVENTION

In some variations, the invention provides an apparatus for real-time monitoring of voltage and differential voltage of both anode and cathode in a metal-ion battery, the apparatus comprising:

a first voltage monitor that is connectable between the anode and a reference electrode of the battery; a second voltage monitor that is connectable between the cathode and the reference electrode or another reference electrode; and a computer programmed using non-transitory memory with executable code for executing the steps of:

receiving anode voltage signals derived from the first voltage monitor;

receiving cathode voltage signals derived from the second voltage monitor;

receiving or calculating a derivative of anode voltage with respect to time and/or a derivative of anode voltage with respect to capacity; and receiving or calculating a derivative of cathode voltage with respect to time and/or a derivative of cathode voltage with respect to capacity.

In some embodiments, the computer is programmed to execute the step of estimating one or more battery states selected from the group consisting of state of charge, state of power, state of health, state of safety, and combinations thereof. In certain embodiments in which the state of charge is estimated, the computer is further programmed to execute the step of estimating anode capacity or anode remaining capacity. In these or other embodiments, the computer is further programmed to execute the step of estimating cathode capacity or cathode remaining capacity.

Some embodiments provide a system in which the apparatus, described above, is linked in operable communication with the battery (such as, but not limited to, a lithium-ion battery).

Some variations of the invention provide an apparatus for real-time assessment of capacity of both anode and cathode in a metal-ion battery, the apparatus comprising:

a first voltage monitor that is connectable between the anode and a reference electrode of the battery; a second voltage monitor that is connectable between the cathode and the reference electrode or another reference electrode; and a computer programmed using non-transitory memory with executable code for executing the steps of:

receiving anode voltage signals derived from the first voltage monitor at a plurality of times;

receiving cathode voltage signals derived from the second voltage monitor at the plurality of times;

receiving current signals derived from battery current at the plurality of times;

estimating, at a first time and a second time, first and second anode open-circuit voltages and correlating the first and second anode open-circuit voltages to first and second anode states of charge, respectively;

calculating anode capacity as the integral of the current signals from the first time to the second time, divided by the difference between the second and first anode states of charge;

estimating, at the first time and a second time, first and second cathode open-circuit voltages and correlating the first and second cathode open-circuit voltages to first and second cathode states of charge, respectively; and calculating cathode capacity as the integral of the current signals from the first time to the second time, divided by the difference between the second and first cathode states of charge.

In some embodiments, the first and second times are selected such that the battery current is about 0. The first and second anode open-circuit voltages may each be estimated from anode voltage at the first and second times, when the battery current is about 0. Also, the first and second cathode open-circuit voltages may each be estimated from cathode voltage at these first and second times.

In some embodiments, the first and second anode open-circuit voltages are correlated to the first and second anode states of charge using a look-up table, graph, equation, or combination thereof. In these or other embodiments, the first and second cathode open-circuit voltages are correlated to the first and second cathode states of charge using a look-up table, graph, equation, or combination thereof.

Some embodiments provide a system in which the apparatus for real-time assessment of capacity of both anode and cathode in a metal-ion battery, is linked in operable communication with the battery (such as, but not limited to, a lithium-ion battery).

Variations of the invention also provide a method of real-time monitoring of voltage and differential voltage of both anode and cathode in a metal-ion battery, the method comprising:

providing a first voltage monitor connected between the anode and a reference electrode of the battery;

providing a second voltage monitor connected between the cathode and the reference electrode or another reference electrode;

providing a computer in operable communication with the battery;

receiving, in the computer, anode voltage signals derived from the first voltage monitor;

receiving, in the computer, cathode voltage signals derived from the second voltage monitor;

receiving or calculating, in the computer, a derivative of anode voltage with respect to time and/or a derivative of anode voltage with respect to capacity; and receiving or calculating, in the computer, a derivative of cathode voltage with respect to time and/or a derivative of cathode voltage with respect to capacity.

In some embodiments, the method further comprises estimating, in the computer, one or more battery states selected from the group consisting of state of charge, state of power, state of health, state of safety, and combinations thereof When the state of charge is estimated, the method may further comprise estimating, in the computer, anode capacity or anode remaining capacity. Also, when the state of charge is estimated, the method may further comprise estimating, in the computer, cathode capacity or cathode remaining capacity.

In some embodiments, the anode voltage signals and/or the cathode voltage signals are compared, in the computer, to predetermined voltage safety limits of the anode and/or the cathode, respectively. In these or other embodiments, the anode and/or cathode voltage derivative with respect to time or with respect to capacity are/is compared, in the computer, to predetermined differential voltage safety limits of the anode and/or the cathode, respectively.

Some variations provide a method of real-time assessment of capacity of both anode and cathode in a metal-ion battery, the method comprising:

providing a first voltage monitor connected between the anode and a reference electrode of the battery;

providing a second voltage monitor connected between the cathode and the reference electrode or another reference electrode;

providing a computer in operable communication with the battery;

operating the battery with a driving profile;

receiving, in the computer, anode voltage signals derived from the first voltage monitor at a plurality of times;

receiving, in the computer, cathode voltage signals derived from the second voltage monitor at the plurality of times;

receiving, in the computer, current signals derived from battery current at the plurality of times;

estimating, in the computer, at a first time and a second time, first and second anode open-circuit voltages and correlating, in the computer, the first and second anode open-circuit voltages to first and second anode states of charge, respectively;

calculating, in the computer, anode capacity as the integral of the current signals from the first time to the second time, divided by the difference between the second and first anode states of charge;

estimating, in the computer, at the first time and the second time, first and second cathode open-circuit voltages and correlating, in the computer, the first and second cathode open-circuit voltages to first and second cathode states of charge, respectively; and calculating, in the computer, cathode capacity as the integral of the current signals from the first time to the second time, divided by the difference between the second and first cathode states of charge.

In some embodiments, the first and second times are selected such that the battery current is about 0; the first and second anode open-circuit voltages are each estimated, in the computer, from first and second measured anode voltages at the first and second times, respectively. In certain embodiments, the battery current is about 0 for at least 5 minutes prior to recording each of the first and second measured anode voltage as each of the first and second anode open-circuit voltages, respectively.

Similarly, in some embodiments wherein the first and second times are selected such that the battery current is about 0, the first and second cathode open-circuit voltages are each estimated, in the computer, from first and second measured cathode voltages at the first and second times, respectively. In certain embodiments, the battery current is about 0 for at least 5 minutes prior to recording each of the first and second measured cathode voltage as each of the first and second cathode open-circuit voltages, respectively.

The anode capacity may be determined as constant-discharge current multiplied by the time period for discharging anode voltage from its minimum to maximum. The cathode capacity may be determined as constant-discharge current multiplied by the time period for discharging cathode voltage from its minimum to maximum.

In various embodiments, the first and second anode open-circuit voltages are correlated, in the computer, to the first and second anode states of charge using a look-up table, graph, equation, or combination thereof. In these or other embodiments, the first and second cathode open-circuit voltages are correlated, in the computer (or another computer), to the first and second cathode states of charge using a look-up table, graph, equation, or combination thereof.

Some embodiments also sense and respond to variations in temperature. In some embodiments, the method further comprises receiving, in the computer, battery temperature signals at the plurality of times. The first and second anode open-circuit voltages are optionally correlated, in the computer, to the first and second anode states of charge using a look-up table, graph, equation, or combination thereof which accounts for variation of anode state of charge with temperature.

Similarly, in some embodiments, the method further comprises receiving, in the computer, battery temperature signals at the plurality of times. The first and second cathode open-circuit voltages are optionally correlated to the first and second cathode states of charge using a look-up table, graph, equation, or combination thereof which accounts for variation of anode state of charge with temperature.

DETAILED DESCRIPTION OF EMBODIMENTS OF THE INVENTION

Figure 1A:
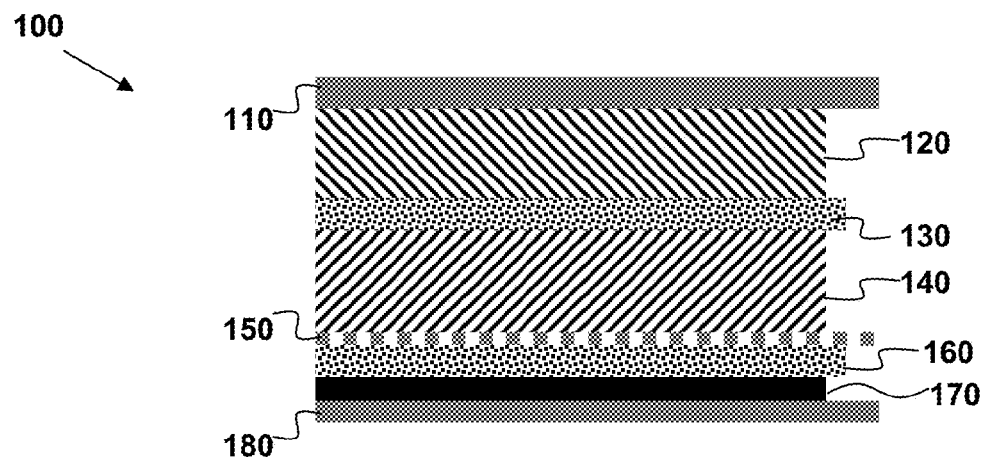
FIG. 1A shows a schematic of a metal-ion battery with a reference electrode that can provide accurate monitoring of cathode and anode under battery operation, in some embodiments.

The methods, apparatus, and systems of the present invention will be described in detail by reference to various non-limiting embodiments and figures.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with the accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. As intended herein, "receiving" shall be broadly construed as including "providing," "sensing" (e.g., using a sensor attached to a computer), "calculating" (e.g., using executable code in a computer), and so on.

Unless otherwise indicated, all numbers expressing parameters, conditions, results, and so forth used in the specification and claims are to be understood as being modified in all instances by the term "about." Accordingly, unless indicated to the contrary, the numbers set forth in the following specification and attached claims are approximations that may vary depending upon specific algorithms and calculations.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of"

Some variations of this invention provide a new method to monitor the health and capacity of the cathode (positive electrode) and, independently, the anode (negative electrode) during battery operation (charge and discharge). At least one reference electrode is part of a management system that monitors the potentials (i.e. voltage) along with the first differential voltage of both electrodes independently, to determine the battery state of capacity and state of health.

In a conventional electrochemical cell (battery), at a given state-of-charge (SOC), the measured cell voltage represents the voltage difference between the cathode and anode:

$$V_{cell} = V_{cathode} - V_{anode} \qquad \text{(EQ. 1)}$$

However, the voltage behavior of each individual electrode is largely unknown since the deconvolution of the full cell voltage to obtain the voltage of each electrode is especially challenging during battery operation.

In a three-electrode cell, for example, voltage monitoring may be used to mitigate damage to the electrodes when the voltage (or voltage rate of change) of the individual electrodes exceeds a threshold value. The derivatives of the potential may be used to reveal potential problems in the electrochemical behavior before the electrodes are damaged. By providing an early indication of a potential problem, the system can respond with the appropriate change in cycling conditions (e.g. reducing the rate or lowering the cycling limits) to avoid damage to the electrode. In addition, this system may also be used to determine the capacity of each electrode independently to better track the health and remaining life of the battery.

In a typical battery, the management system relies only on the voltage from the full cell (no reference electrode). However, the full cell voltage is a poor indicator of the health of each electrode itself. Some variations provide a simple, direct method of monitoring the voltage (V) and either or both of derivative of the voltage with respect to capacity (dV/dQ) or derivative of the voltage with respect to time (dV/dt) of each electrode independently, in a battery using a reference electrode (e.g., in a three-electrode cell). Improved battery management and a safer battery can result. The capacity Q is the capacity of the battery electrode, measured in coulombs.

A three-electrode cell equipped with a system to monitor the voltage and differential voltage can provide critical information to the battery management system. The system can respond by adjusting the limits and rates used in the charge/discharge reactions (optimizing electrochemical performance) and extending the battery life. Also, by monitoring the voltage and differential voltage of each of the electrodes independently, limits can be established below threshold values where damage occurs.

As a battery ages, the voltages of the positive and negative electrodes diverge due to resistance rise and material degradation. For example, during battery charging, the voltage of the negative electrode is depressed to a lower voltage close to 0 V, while the positive electrode voltage can rise higher quickly due to the increase in resistance as the battery ages. In this common scenario, the full cell voltage often appears normal while the actual voltages of each of the electrodes are outside the safety limits. Changes in the voltage profiles due to cell aging are very difficult to quantify from the terminal voltage of the full cell.

The disclosed invention in some variations enables the monitoring of the individual electrode voltage and the rate of voltage change with time (dV/dt) or with capacity (dV/dQ) for enhanced battery performance and safety. While the direct monitoring of each individual electrode voltage is useful for identifying when a battery has reached or exceeded a safety limit, monitoring the change in voltage (dV/dQ), along with the voltage (V), provides more useful inputs for a battery management system (BMS). Monitoring V and dV/dQ (or dV/dt) provides an early warning system, identifying when the voltage is approaching a limit and allowing the BMS to make a change to the battery operation so the limits are never reached. The differential voltage is especially sensitive to changes in the material. As the battery electrode degrades, the magnitudes of the peaks in the dV/dQ spectrum tend to increase. Therefore dV/dQ is a reliable indicator of the battery state-of-health.

Some embodiments are premised on the realization that the magnitude of the dV/dQ change at a specific state-of-charge (SOC) can be used to indicate and predict the capacity of the battery. The differential voltage (dV/dt or dV/dQ) can also be used (with the voltage) in a battery management system to actively control the battery operation (cycling rate, depth of discharge, and/or depth of charge) to ensure optimal battery performance and safety. For example, during charging, when the electrode voltage is near the safety limit and approaching quickly, the BMS can be programmed to reduce the charging current to safeguard the battery while maximizing the charge capacity.

In some variations, the invention provides a method of determining the capacity (online) of each electrode over the life of the battery, which is useful for accurate state-of-charge and state-of-power determination, among other things. This information can also be used in a battery management system to maintain optimal cycling (within the safety limits) and to determine the remaining life of the battery.

Embodiments of the invention can improve battery diagnosis and battery management systems. Examples include improving battery state-of-charge (SOC) monitoring, enhancing battery safety, monitoring battery aging, and extending battery life. Battery states include, but are not limited to, state-of-health, state-of-charge, state-of-power, high-frequency resistance, charge-transfer resistance, and double-layer capacitance. State-of-health is a figure of merit of the condition of a battery (or a cell, or a battery pack), compared to its ideal conditions. State-of-charge is an indication of how much useful energy remains in the battery. State-of-power characterizes the charge and discharge power capabilities of the battery.

Embodiments of the present invention will now be described in detail, including reference to the accompanying figures. The figures provide representative illustration of the invention and are not limiting in their content. It will be understood by one of ordinary skill in the art that the scope of the invention extends beyond the specific embodiments depicted. For example, the invention is by no means limited to lithium-ion batteries.

Without a reference electrode, only the full cell battery voltage information is available. During battery operation, even when the battery voltage appears to be in a normal operating window, it is difficult to control the positive and negative electrode potentials within safety limits. There are several scenarios by which not knowing the individual electrode voltages can lead to potential shortcomings and serious safety concerns:

1. During charging, the negative electrode (anode) can drop below 0 V (vs. Li), causing lithium plating and ultimately an internal short circuit.

2. During charging, the positive electrode (cathode) can over-charge beyond the safety limit, causing decomposition of the active materials and electrolytes creating an excess of heat and possible thermal runaway.

3. During discharging, the negative electrode voltage can rise above voltage safety limit, causing dissolution of metal ions from the current collector and an internal short circuit.

4. During discharging, the positive electrode voltage can drop below the voltage safety limit, causing over-discharging of positive active materials.

Figure 1B:
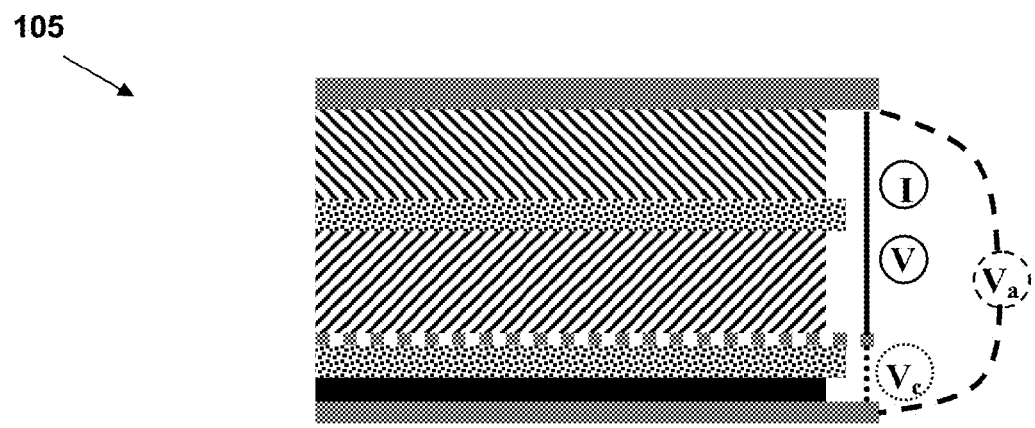
FIG. 1B depicts circuit connections that may be supplied to the metal-ion battery of FIG. 1B, in some embodiments.

It is therefore preferred to include at least one reference electrode in the battery configuration. FIGS. 1A and 1B depict an exemplary three-electrode cell, in some embodiments of a metal-ion battery with a reference electrode that can provide accurate monitoring of cathode and anode potentials under battery operation. The configuration includes a negative electrode material on metal foil, a positive electrode material on metal mesh, and a metal reference electrode on metal foil. Each electrode is electronically isolated by separators. In some embodiments of FIG. 1A, for example, the battery structure 100 is in a layered configuration. A cathode 140 coated on a porous aluminum (Al) mesh (porous) current collector 150 faces an anode 120 coated on a copper (Cu) current collector 110 separated by a separator layer 130. The porous current collector 150 enables ion communication through the cathode. A reference electrode 170 (for example, lithium on copper foil 180) is disposed adjacent to the cathode 140 with Al mesh current collector 150. The reference electrode 170 is electronically isolated from the other electrodes by a separator layer 160. The anode 120 and cathode 140 may be switched, if desired.

The battery structure 105 of FIG. 1B depicts circuit connections that may be adapted to the battery structure 100. A current source/monitor (labeled with a circled I) and a voltage monitor (labeled with a circled V) are connected between the anode's Cu current collector 110 and the cathode's Al current collector 150. Another voltage monitor (labeled $V_a$ with dashed lines) is connected between the anode's Cu current collector 110 and the reference electrode's Cu foil current collector 180. Another voltage monitor (labeled $V_c$ with dotted lines) is connected between the cathode's Al current collector 150 and the reference electrode's Cu foil current collector 180. The battery is driven with a current I cycling profile, and measurement is made in real time of the current I and voltage V between anode and cathode, as well as the anode potential $V_a$ referring to the reference electrode and/or the cathode potential $V_c$ referring to the reference electrode. It is noted that one of the voltage monitors in FIG. 1B is redundant but may be employed to verify the data. That is, only two of the voltage monitors (V, $V_a$, $V_c$) are necessary.

Some variations of the invention provide circuit connections in systems and apparatus, and associated methods, that can characterize a three-electrode battery in real time. The proposed circuit connection enables measurement of both anode and cathode potential, sampling them concurrently without interference.

In this disclosure, "real time" is intended to mean that characterization (including monitoring and updating) has a time scale of about 1 millisecond ($10^{-3}$ s) or less. Any event happening within about 1 millisecond is considered as happening at the same time, with respect to battery monitoring. Therefore, battery characterization within about 1 millisecond is considered real-time (or delay-free) characterization. The actual time scale of characterization may on the order of $10^{-4}$ s, $10^{-5}$ s, $10^{-6}$ s, or even shorter times, in some embodiments.

It should be noted that many other battery configurations are possible. For example, the reference electrode may be disposed perpendicular to the anode and cathode layers, on the side. A wire reference electrode may be supplied. Generally, various shapes, positions, and types of reference electrodes may be used. Also, more than one reference electrode may be employed. In some embodiments, a reference electrode is supplied for the anode, and another reference electrode is supplied for the cathode. A spare electrode may also be included which may function as either a reference electrode or as a backup anode or cathode, if needed.

In some variations, the invention provides an apparatus for real-time monitoring of voltage and differential voltage of both anode and cathode in a metal-ion battery, the apparatus comprising:

a first voltage monitor that is connectable between the anode and a reference electrode of the battery; a second voltage monitor that is connectable between the cathode and the reference electrode or another reference electrode; and a computer programmed using non-transitory memory with executable code for executing the steps of:

receiving anode voltage signals derived from the first voltage monitor;

receiving cathode voltage signals derived from the second voltage monitor;

receiving or calculating a derivative of anode voltage with respect to time and/or a derivative of anode voltage with respect to capacity; and receiving or calculating a derivative of cathode voltage with respect to time and/or a derivative of cathode voltage with respect to capacity.

In some embodiments, the computer is programmed to execute the step of estimating one or more battery states selected from the group consisting of state of charge, state of power, state of health, state of safety, and combinations thereof. In certain embodiments in which the state of charge is estimated, the computer is further programmed to execute the step of estimating anode capacity or anode remaining capacity. In these or other embodiments, the computer is further programmed to execute the step of estimating cathode capacity or cathode remaining capacity.

Some embodiments provide a system in which the apparatus, described above, is linked in operable communication with the battery (such as, but not limited to, a lithium-ion battery).

In some variations, the invention provides a method of characterizing a metal-ion battery (e.g., a lithium-ion battery) in real time, the method comprising:

(a) providing or obtaining a battery with a first electrode, a second electrode, and a reference electrode;

(b) conducting at least two of the following substeps: (b)(i) providing a first voltage monitor connected between the first electrode and the second electrode; (b)(ii) providing a second voltage monitor connected between the first electrode and the reference electrode; and/or (b)(iii) providing a third voltage monitor connected between the second electrode and the reference electrode;

(c) driving the battery, using a current source connecting the first and second electrodes, with any current cycling profile;

(d) measuring, in real time, current signals between the first and second electrodes and at least two voltage signals derived from the first, second, and/or third voltage monitors in substeps (b)(i), (b)(ii), and/or (b)(iii), respectively; and (e) optionally measuring, in real time, at least two voltage derivatives (with respect to capacity or with respect to time) derived from the first, second, and/or third voltage monitors in substeps (b)(i), (b)(ii), and/or (b)(iii), respectively.

In some embodiments, all of substeps (b)(i), (b)(ii), and (b)(iii) are conducted. Optionally, in these embodiments, one of the voltage monitors may be repositioned for use as another one of the voltage monitors.

In other variations, the invention provides a battery system comprising a three-electrode metal-ion battery configured with at least two voltage monitors selected from a first voltage monitor connected between a first electrode and a second electrode, a second voltage monitor connected between the first electrode and a reference electrode, and/or a third voltage monitor connected between the second electrode and the reference electrode; a current source connecting the first and second electrodes; and a computer disposed in communication with the battery, the computer programmed using non-transitory memory with executable code for executing the steps of:

(a) controlling the current source to drive the battery with a current cycling profile;

(b) measuring current signals between the first and second electrodes, and at least two voltage signals derived from the first, second, and/or third voltage monitors; and (c) measuring at least two voltage derivatives (with respect to capacity or with respect to time) derived from the first, second, and/or third voltage monitors.

Some variations of the invention provide an apparatus for real-time assessment of capacity of both anode and cathode in a metal-ion battery, the apparatus comprising:

a first voltage monitor that is connectable between the anode and a reference electrode of the battery; a second voltage monitor that is connectable between the cathode and the reference electrode or another reference electrode; and a computer programmed using non-transitory memory with executable code for executing the steps of:

receiving anode voltage signals derived from the first voltage monitor at a plurality of times;

receiving cathode voltage signals derived from the second voltage monitor at the plurality of times;

receiving current signals derived from battery current at the plurality of times;

estimating, at a first time and a second time, first and second anode open-circuit voltages and correlating the first and second anode open-circuit voltages to first and second anode states of charge, respectively;

calculating anode capacity as the integral of the current signals from the first time to the second time, divided by the difference between the second and first anode states of charge;

estimating, at the first time and a second time, first and second cathode open-circuit voltages and correlating the first and second cathode open-circuit voltages to first and second cathode states of charge, respectively; and calculating cathode capacity as the integral of the current signals from the first time to the second time, divided by the difference between the second and first cathode states of charge.

In some embodiments, the first and second times are selected such that the battery current is about 0 (such as less than 0.01 A, 0.005 A, 0.004 A, 0.003 A, 0.002 A, or 0.001 A). The first and second anode open-circuit voltages may each be estimated from anode voltage at the first and second times, when the battery current is about 0 (such as less than 0.01 A, 0.005 A, 0.004 A, 0.003 A, 0.002 A, or 0.001 A). Also, the first and second cathode open-circuit voltages may each be estimated from cathode voltage at these first and second times.

In some embodiments, the first and second anode open-circuit voltages are correlated to the first and second anode states of charge using a look-up table, graph, equation, or combination thereof. In these or other embodiments, the first and second cathode open-circuit voltages are correlated to the first and second cathode states of charge using a look-up table, graph, equation, or combination thereof.

Some embodiments provide a system in which the apparatus for real-time assessment of capacity of both anode and cathode in a metal-ion battery, is linked in operable communication with the battery (such as, but not limited to, a lithium-ion battery).

Variations of the invention also provide a method of real-time monitoring of voltage and differential voltage of both anode and cathode in a metal-ion battery, the method comprising:

providing a first voltage monitor connected between the anode and a reference electrode of the battery;

providing a second voltage monitor connected between the cathode and the reference electrode or another reference electrode;

providing a computer in operable communication with the battery;

receiving, in the computer, anode voltage signals derived from the first voltage monitor;

receiving, in the computer, cathode voltage signals derived from the second voltage monitor;

receiving or calculating, in the computer, a derivative of anode voltage with respect to time and/or derivative of anode voltage with respect to capacity; and receiving or calculating, in the computer, a derivative of cathode voltage with respect to time and/or a derivative of cathode voltage with respect to capacity.

In some embodiments, the method further comprises estimating, in the computer, one or more battery states selected from the group consisting of state of charge, state of power, state of health, state of safety, and combinations thereof.

When the state of charge is estimated, the method may further comprise estimating, in the computer, anode capacity or anode remaining capacity. Also, when the state of charge is estimated, the method may further comprise estimating, in the computer, cathode capacity or cathode remaining capacity.

In some embodiments, the anode voltage signals and/or the cathode voltage signals are compared, in the computer, to predetermined voltage safety limits of the anode and/or the cathode, respectively. In these or other embodiments, the anode and/or cathode voltage derivative with respect to time or with capacity are/is compared, in the computer, to predetermined differential voltage safety limits of the anode and/or the cathode, respectively.

Some variations provide a method of real-time assessment of capacity of both anode and cathode in a metal-ion battery, the method comprising:

providing a first voltage monitor connected between the anode and a reference electrode of the battery;

providing a second voltage monitor connected between the cathode and the reference electrode or another reference electrode;

providing a computer in operable communication with the battery;

operating the battery with a driving profile;

receiving, in the computer, anode voltage signals derived from the first voltage monitor at a plurality of times;

receiving, in the computer, cathode voltage signals derived from the second voltage monitor at the plurality of times;

receiving, in the computer, current signals derived from battery current at the plurality of times;

estimating, in the computer, at a first time and a second time, first and second anode open-circuit voltages and correlating, in the computer, the first and second anode open-circuit voltages to first and second anode states of charge, respectively;

calculating, in the computer, anode capacity as the integral of the current signals from the first time to the second time, divided by the difference between the second and first anode states of charge;

estimating, in the computer, at the first time and the second time, first and second cathode open-circuit voltages and correlating, in the computer, the first and second cathode open-circuit voltages to first and second cathode states of charge, respectively; and calculating, in the computer, cathode capacity as the integral of the current signals from the first time to the second time, divided by the difference between the second and first cathode states of charge.

In some embodiments, the first and second times are selected such that the battery current is about 0 (such as less than 0.01 A, 0.005 A, 0.004 A, 0.003 A, 0.002 A, or 0.001 A); the first and second anode open-circuit voltages are each estimated, in the computer, from first and second measured anode voltages at the first and second times, respectively. In certain embodiments, the battery current is about 0 for at least 1, 2, 3, 4, 5, 6, 7, 8, 9, or 10 minutes prior to recording each of the first and second measured anode voltage as each of the first and second anode open-circuit voltages, respectively.

Similarly, in some embodiments wherein the first and second times are selected such that the battery current is about 0 (such as less than 0.01 A, 0.005 A, 0.004 A, 0.003 A, 0.002 A, or 0.001 A), the first and second cathode open-circuit voltages are each estimated, in the computer, from first and second measured cathode voltages at the first and second times, respectively. In certain embodiments, the battery current is about 0 for at least 1, 2, 3, 4, 5, 6, 7, 8, 9, or 10 minutes prior to recording each of the first and second measured cathode voltage as each of the first and second cathode open-circuit voltages, respectively.

The anode capacity may be determined as constant-discharge current multiplied by the time period for discharging anode voltage from its minimum to maximum. The cathode capacity may be determined as constant-discharge current multiplied by the time period for discharging cathode voltage from its minimum to maximum.

In various embodiments, the first and second anode open-circuit voltages are correlated, in the computer, to the first and second anode states of charge using a look-up table, graph, equation, or combination thereof. In these or other embodiments, the first and second cathode open-circuit voltages are correlated, in the computer (or another computer), to the first and second cathode states of charge using a look-up table, graph, equation, or combination thereof.

In certain embodiments, additional data inputs (beyond current and voltage) are considered in the model and algorithms. Additional data inputs may relate to ambient conditions of the local environment, including temperature, relative humidity, and electromagnetic interference patterns, for instance. Additional data inputs may be based on previous experience with similar devices, or other ways to capture prior knowledge to improve the accuracy of the diagnostics for the intended purpose. These additional data inputs may be quantitative or qualitative in nature.

Some embodiments also sense and respond to variations in temperature. In some embodiments, the method further comprises receiving, in the computer, battery temperature signals at the plurality of times. The first and second anode open-circuit voltages are optionally correlated, in the computer, to the first and second anode states of charge using a look-up table, graph, equation, or combination thereof which accounts for variation of anode state of charge with temperature.

Similarly, in some embodiments, the method further comprises receiving, in the computer, battery temperature signals at the plurality of times. The first and second cathode open-circuit voltages are optionally correlated, in a computer, to the first and second cathode states of charge using a look-up table, graph, equation, or combination thereof which accounts for variation of anode state of charge with temperature.

Certain embodiments of real-time assessment of capacity of both anode and cathode in a metal-ion battery utilize the following exemplary procedure:

(a) An open-circuit voltage (OCV)-state of charge (SOC) lookup table is measured for each electrode of a battery with a reference electrode. The minimum and maximum voltage range of the electrode is established to define the SOC range.

(b) The total capacity of each electrode (i.e., anode's $Ah_{a\_nominal}$ and cathode's $Ah_{c\_nominal}$) is determined by $I \times (t_{end} - t_0)$, where I equals the constant discharge current, and $(t_{end} - t_0)$ is the time period for discharging the anode (or cathode) voltage from its minimum to maximum.

(c) The battery is operated with any driving profile and the current, anode voltage, cathode voltage, and optionally temperature of the battery are measured as a function of time.

(d) The zero-current instants are identified during the cycling process. If the zero-current period lasts longer than five minutes, the measured electrode voltage at the end of the zero-current period is recorded as the OCV of the corresponding electrode.

(e) The SOCs of each electrode are determined using the measured OCVs and the SOC-OCV lookup table.

(f) Each electrode's capacity, $Ah_c$ and $Ah_a$, is calculated.

If the battery is used at different temperatures (such as a temperature variation of at least 5° C. or 10° C.), lookup tables are acquired for temperature different ranges (e.g., for every 5° C. or 10° C.). The lookup tables for each electrode, under different temperatures or temperature ranges, are saved and used to later determine the SOCs.

The primary functional components of a typical lithium-ion battery are the anode, cathode, and electrolyte, in which a lithium ion moves between the anode and cathode in the electrolyte. A separator is used to separate cathode and anode to prevent electron shortage. Current collectors, normally metal, are used to collect electrons from both cathode and anode. The lithium ion moves from the anode to the cathode during discharge and from the cathode to the anode when charging.

Both the anode and cathode are materials into which and from which lithium can migrate. The process of lithium moving into the anode or cathode is referred to as insertion (or intercalation), and the reverse process, in which lithium moves out of the anode or cathode is referred to as extraction (or deintercalation).

In the battery system of certain embodiments, the first electrode is disposed adjacent to a first current collector, wherein the first electrode supplies or accepts selected battery metal ions; the second electrode, with polarity opposite of the first electrode, is disposed adjacent to a second current collector, wherein the second electrode supplies or accepts the metal ions, and wherein the second current collector is porous and permeable to the metal ions; the reference electrode is disposed adjacent to a third current collector, wherein the reference electrode contains the metal ions; a first separator is interposed between the first electrode and the second electrode, to electronically isolate the first electrode from the second electrode; and a second separator is interposed between the second current collector and the reference electrode, to electronically isolate the second electrode from the reference electrode.

Each of the first, second, and third voltage monitors is present in the battery system, in certain embodiments. An external reference circuit may be electrically connected to a monitor to display or record voltage of each electrode.

Some embodiments of the invention utilize battery configurations that enable accurate in situ monitoring of the potentials of the cathode (positive electrode) and anode (negative electrode) under actual operation of a lithium-ion battery. In such configurations, a third electrode is incorporated as a reference electrode. Porous current collectors allow the communication of ions through the backside (away from the direct ion paths between the cathode and anode) where a reference electrode is inserted. The reference electrode is electronically isolated using one or more separators.

In some embodiments, the metal-ion battery is a lithium-ion battery in which the reference electrode is not spatially between the first and second electrodes.

Battery capacity is primarily determined by the amount of active lithium traveling between the anode and the cathode. When the battery is charged for the first time, lithium leaves the cathode and enters the anode. After all removable lithium leaves the cathode, only part of that lithium is active in the anode because some lithium will typically be lost to form a solid-state electrolyte interface on the anode surface. During subsequent battery cycles, the amount of active lithium will be smaller than the storage capacity of both the cathode and the anode. Consequently, lithium battery capacity is usually equal to the amount of active lithium. Corrosion of this active lithium during the life of the battery leads directly to capacity loss.

The cathode and anode should be electronically separated by a separator, but ionically connected with electrolyte. Reference electrodes with large surface areas may be utilized, to minimize polarization resistance. In addition, the reference electrode may be disposed very close to the target electrodes, to minimize IR drop while avoiding the shielding effect. An IR drop is caused when a reference electrode is too far away from the target electrodes. The shielding effect is caused when a reference electrode blocks the current pathways between the positive and negative electrodes.

While the addition of the reference electrode can slightly reduce the overall cell energy density, this reduction will be compensated for by the benefits gain from dramatically improved battery health monitoring and battery safety.

Conventional reference electrodes suffer from two fundamental issues that compete with each other: (i) the reference electrode needs to be as close as possible to the target electrode to minimize the IR drop; (ii) conversely, the reference electrode needs to far enough from the target electrode to avoid a shielding effect that distorts the electrical current path between the cathode and anode.

The conventional wisdom is to use very thin wires (e.g., submicron in diameter) to reduce the shielding effect while getting closer to the target electrode. However, thin-wire reference electrodes often are associated with large polarization resistance. To avoid the distortion of the current pathways, some known designs place the reference electrode on the edge or the cross section of the battery electrodes, outside of the current path between the cathode and anode; however, the voltage readings may not be accurate due to edge effects and voltage interference.

The aforementioned limitations can be mitigated by a battery configuration such as that illustrated in FIG. 1A, discussed above. Incorporation of a reference electrode can provide accurate monitoring of cathode and anode potentials under battery operation. The configuration includes a negative electrode material on copper foil, a positive electrode material on aluminum mesh, and a lithium metal reference electrode on copper foil. Each electrode is electronically isolated by separators. When soaked in an organic electrolyte, the structure of FIG. 1A enables direct ion communication between the reference electrode and the cathode and anode, without blocking the current pathways of the battery. Note that the positions of the anode and cathode may be switched in alternative embodiments.

During normal battery operation, current is flowing between the cathode and anode. The voltage monitors are used to monitor potentials as described above. With reference to FIG. 1A, the voltage between current collectors 110 and 150 is the normal battery voltage. The voltage between current collectors 110 and 180 is the anode voltage. The voltage between current collectors 150 and 180 is the cathode voltage. Subtraction of the cathode voltage from the anode voltage gives the battery voltage.

In addition, a very small current may optionally be applied between the cathode and a reference electrode and/or between the anode and a reference electrode (which may be a different reference electrode than the cathode's reference electrode), during battery operation, in certain embodiments. Such reference current is preferably less than about $10^{-6}$ amp, such as about $10^{-7}$ amp, $10^{-8}$ amp, $10^{-9}$ amp, or less.

The reference electrode may be rather large in terms of its "projected area," which means the geometric area of the surface as projected toward the anode or cathode. The reference electrode may have a reference-electrode projected area that is at least about 10%, 20%, 30%, 40%, 50%, 60%, 70%, 80%, 90%, 100% or more of the projected area of the anode and/or the cathode.

The surface area of a reference electrode may vary widely, such as from about 1 mm² to about 10 cm² or more. In some embodiments, the area of the reference electrode is as large as the actual size of the working electrode, such as its projection area.

The porous current collector 150 (FIG. 1A) may be characterized by an average pore size from about 1 nm to about 10 μm, such as about 2 nm, 3 nm, 5 nm, 8 nm, 10 nm, 15 nm, 20 nm, 30 nm, 50 nm, 75 nm, 100 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, or 9 μm.

The porous current collector 150 may be characterized by an average pore-to-surface ratio (in two dimensions) or porosity (in three dimensions) from about 0.1% to about 99.9%, such as about 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99%. In some embodiments, the average pore-to-surface ratio or porosity is at least 1%, 5%, 10%, 15%, or 20%.

In preferred embodiments, the metal ions are lithium ions. The anode 120 material must be capable of incorporating lithium ions during battery charging, and then releasing the lithium ions during battery discharge. Exemplary anode 120 materials suitable for the present invention include, but are not limited to, carbon materials such as graphite, coke, soft carbons, and hard carbons; and metals such as Si, Al, Sn, or alloys thereof. Other exemplary anode 120 materials include titanium oxides, germanium, copper/tin, and lithium compounds containing metal oxides, such as oxides of W, Fe, and Co. Anodes 120 can also include fillers and binders. The anode 120 material preferably exhibits long cycle life and calendar life, and does not experience significant resistance increase throughout the life of the battery.

Preferably, the anode 120 material consists essentially of graphitic carbon or another electron-conducting carbon. Some examples of electron-conducting carbon include natural graphites, such as flaky graphite, plate-like graphite, and other types of graphite; high-temperature sintered carbon products obtained, for example, from petroleum coke, coal coke, celluloses, saccharides, and mesophase pitch; artificial graphites, including pyrolytic graphite; carbon blacks, such as acetylene black, furnace black, Ketjen black, channel black, lamp black, and thermal black; asphalt pitch, coal tar, active carbon, mesophase pitch, and polyacetylenes.

The cathode 140 material must be capable of supplying lithium ions during battery charging, and then incorporating the lithium ions during battery discharge. The cathode 140 material can be, for example, a lithium metal oxide, phosphate, or silicate. Exemplary cathode materials suitable for the present invention include, but are not limited to, $LiMO_2$ (M=Co, Ni, Mn, or combinations thereof); $LiM_2O_4$ (M=Mn, Ti, or combinations thereof); $LiMPO_4$ (M=Fe, Mn, Co, or combinations thereof); and $LiM_xM'_{2-x}O_4$ (M, M'=Mn or Ni). The cathode 140 material preferably exhibits long cycle life and calendar life, and does not experience significant resistance increase throughout the life of the battery.

The cathode 140 may further include one or more conductive fillers to provide enhanced electronic conductivity. Examples of conductive fillers include, but are not limited to, conductive carbons, graphites, activated carbon fibers, non-activated carbon nanofibers, metal flakes, metal powders, metal fibers, carbon fabrics, metal mesh, and electrically conductive polymers. The cathode 140 may also further comprise other additives such as, for example, alumina, silica, and transition-metal chalcogenides.

The cathode 140 may also include a binder. The choice of binder material may vary widely so long as it is inert with respect to the other materials in the cathode. Useful binders are materials, usually polymeric, that allow for ease of processing of battery electrode composites and are generally known to those skilled in the art of electrode fabrication. Examples of useful binders include, but are not limited to, polytetrafluoroethylenes, polyvinylidene fluorides, ethylene-propylene-diene rubbers, polyethylene oxides, acrylates, methacrylates, divinyl ethers, and the like.

The reference electrode 170 material may vary widely. Preferably the reference electrode 170 material is stable over the life of the battery, and exhibits a known reference voltage. In preferred embodiments, the reference electrode 170 material possesses a flat voltage profile, i.e., the voltage does not change substantially at different states of charge.

The reference electrode 170 material may include one or more lithium-containing materials. Exemplary lithium-containing reference electrode materials include, but are not limited to, lithium metal, $LiMO_2$ (M=Co, Ni, Mn, or combinations thereof); $LiM_2O_4$ (M=Mn, Ti, or combinations thereof); $LiMPO_4$ (M=Fe, Mn, Co, or combinations thereof); and $LiM_xM'_{2-x}O_4$ (M, M'=Mn or Ni). Lithium-containing reference electrode materials may include lithium alloys of metals such as Si, Al, and Sn. Other exemplary lithium-containing reference electrode materials include lithium-containing compounds of carbon materials such as graphite, coke, soft carbons, and hard carbons. In certain embodiments, the reference electrode 170 material is selected from the group consisting of metallic lithium, lithium titanium oxide, lithium iron phosphate, lithiated silicon, and combinations thereof Current collectors 110 and 180 collect electrical current generated and provide an efficient surface for attachment of electrical contacts leading to the external circuit. The current collectors 110 and 180 may be made from any suitable materials, such as (but not limited to) Al, Cu, Ni, C, Ti, Au, or Pt. The current collectors 110 and 180 may also be fabricated from alloys, such as stainless steel. Some embodiments employ conducting carbonaceous materials for current collectors 110 and 180. Current collectors 110 and 180 may be porous or non-porous, such as 5-50 μm thick metal foils.

Current collector 150 also collects electrical current generated and provides an efficient surface for attachment of electrical contacts leading to the external circuit. The current collector 150 is porous to allow ion communication through the cathode 140 (or another electrode, in other embodiments). A porous current collector allows lithium ions to be transported through the material, in the direction of ion flow. Preferred forms of porous current collectors 150 include, but are not limited to, mesh, foam, grids, nets, woven fibers, honeycombs, patterned or perforated holes on metal foil, metallized plastic films, expanded metal grids, metal wools, woven carbon fabrics, woven carbon meshes, non-woven carbon meshes, and carbon felts, and structured patterns such as micro-trusses. The pore size in porous current collectors 150 may vary, such as from about 1 nm to about 10 μm. Pores may be imparted into current collectors by etching or some other means. The holes may be round, square, or some other shape.

In some embodiments, one or more electrodes are free-standing and able to conduct electrons to or from an external circuit that is attached to the electrode. For such free-standing electrodes, a distinct current collector adjacent to the electrode is not necessary. For example, with reference to FIG. 1, current collector 110 and/or current collector 180 are not present in some embodiments employing a free-standing anode 120 and/or a free-standing reference electrode 170, respectively.

Some embodiments utilize a three-electrode battery as described in U.S. patent application Ser. No. 13/923,354, filed Jun. 20, 2013, for "BATTERY WITH REFERENCE ELECTRODE FOR VOLTAGE MONITORING" by Wang et al., which is hereby incorporated by reference herein.

Separators can be fabricated from any suitable material. Examples include cellulosic materials (e.g., paper), non-woven fabrics (e.g., cellulose/rayon non-woven fabric), microporous resin films, and porous metal foils. The separator can be an insulating thin film that is high in ion permeability and that has a prescribed mechanical strength. As the material of the separator, an olefin polymer, a fluorine-containing polymer, a cellulose polymer, a polyimide, a nylon, glass fiber, or alumina fiber, in the form of a non-woven fabric, a woven fabric, or a microporous film, may be used.

Lithium-ion batteries include a liquid electrolyte to conduct lithium ions. The liquid electrolyte acts as a carrier between the cathode and the anode when the battery passes an electric current through an external circuit, and also between the lithium reference electrode and the cathode or anode in accordance with this invention. Liquid or gel electrolytes may be employed. The electrolyte may be aqueous or nonaqueous.

The electrolyte generally includes a solvent and a lithium salt (anion plus lithium cation). Examples of the solvent that can be used include aprotic organic solvents, such as propylene carbonate, ethylene carbonate, butylene carbonate, dimethyl carbonate, diethyl carbonate, methyl ethyl carbonate, γ-butyrolactone, methyl formate, methyl acetate, 1,2-dimethoxyethane, tetrahydrofuran, 2-methyltetrahydrofuran, dimethyl sulfoxide, 1,3-dioxolane, formamide, dimethylformamide, dioxolane, dioxane, acetonitrile, nitromethane, ethyl monoglyme, phosphoric triesters, trimethoxymethane, dioxolane derivatives, sulfolane, 3-methyl-2-oxazolidinone, propylene carbonate derivatives, tetrahydrofuran derivatives, ethyl ether, 1,3-propanesultone, N-methyl acetamide, acetonitrile, acetals, ketals, sulfones, sulfolanes, aliphatic ethers, cyclic ethers, glymes, polyethers, phosphate esters, siloxanes, dioxolanes, and N-alkylpyrrolidones. Ethylene carbonate and propylene carbonate are preferable. As is known in the art, other minor components and impurities can be present in the electrolyte composition.

Lithium salts include, but are not limited to, $LiClO_4$, $LiBF_4$, $LiPF_6$, $LiCF_3SO_3$, $LiCF_3CO_2$, $LiAsF_6$, $LiSbF_6$, $LiAlCl_4$, LiCl, LiBr, and LiI, which may be used alone or as a mixture of two or more. $LiBF_4$ and $LiPF_6$ are preferable, in some embodiments. The concentration of the salt is not particularly limited, but preferably is about 0.1 to 5 mol/L of the electrolytic solution.

The amount of electrolytes to be used in the battery may vary. Preferred amounts will depend on the amounts of the cathode and anode active material and the size of the battery.

The battery can be packaged into either prismatic format cells or cylindrical cells. In the prismatic format, the stacked structure is preferably sealed with a packaging material capable of preventing air and water contamination of the battery. Three terminals should be employed to allow electrical access to the battery—terminals for each of the cathode, the anode, and the lithium reference electrode.

In a cylindrical format, a multi-layered structure will be wound into a jelly roll. The lithium reference electrode layer can be placed in the outmost layer, or another layer. The jelly roll can be sealed in a metal container after battery electrolyte is added.

Generally, any of the multi-layered battery structures described herein may be repeated to increase the total capacity of the battery.

In some embodiments, the battery structure includes the reference electrode at one end of stacked layers. In some embodiments, the battery structure includes the reference electrode within stacked layers. The battery structure may be in a cylindrical or wounded prismatic configuration, with a reference electrode as an outer layer of the configuration, an inner layer of the configuration, or both. In certain embodiments, the battery structure further comprises at least one additional reference electrode which may be positioned such that it is not disposed spatially between the first electrode and the second electrode.

Lithium-ion batteries are typically included in a battery pack, which includes a plurality of electrochemical cells that are electrically connected in series and/or in parallel. Lithium-ion battery packs come in many shapes, sizes, capacities, and power ratings, depending on the intended use of the battery pack. Battery packs will typically include a number of lithium-ion cells and a thermal-management system. Open space or a heat-absorbing material may be incorporated between cells, to avoid excessive heating. Or, ceramic plates may be included between each cell, for example. A vent may be added to the battery box in case of thermal runaway reactions. In preferred embodiments utilizing this invention, the engineering overhead for thermal management is reduced by anode/cathode monitoring, thus increasing the effective system energy density.

Lithium-ion batteries according to this invention can be suitable for operating across a variety of temperature ranges. The temperature of lithium-ion battery operation can vary, as is known. Exemplary operation temperatures can be from −50° C. to 80° C., such as for military applications. For computers and related devices, as well as for electric-vehicle applications, an exemplary operation range is −30° C. to 60° C.

The scope of the invention, as mentioned above, is beyond lithium-ion batteries. In particular, the battery electrodes may be based on sodium (Na), potassium (K), or magnesium (Mg), for example. When alternative ions (other than $Li^+$) are employed, the reference electrode material should contain the alternative ions (e.g., $Na^+$, $K^+$, or $Mg^{2+}$).

The "computer" utilized in the apparatus is any programmable computing device, or plurality of devices which may be distributed in time or space, capable of being programmed (such as using C++ programming language) or otherwise caused to execute code for executing the steps of any of the methods or algorithms described herein. The algorithm may be embedded within a controller.

In some embodiments, the computer has a processor, an area of main memory for executing program code under the direction of the processor, a storage device for storing data and program code and a bus connecting the processor, main memory, and the storage device; the code being stored in the storage device and executing in the main non-transient memory under the direction of the processor, to perform the steps of the methods or algorithms recited in this description. Optionally, the computer may be configured to exchange data with a network (such as the Internet), and may carry out calculations on remote computers, servers, or via cloud computing.

Figure 2:
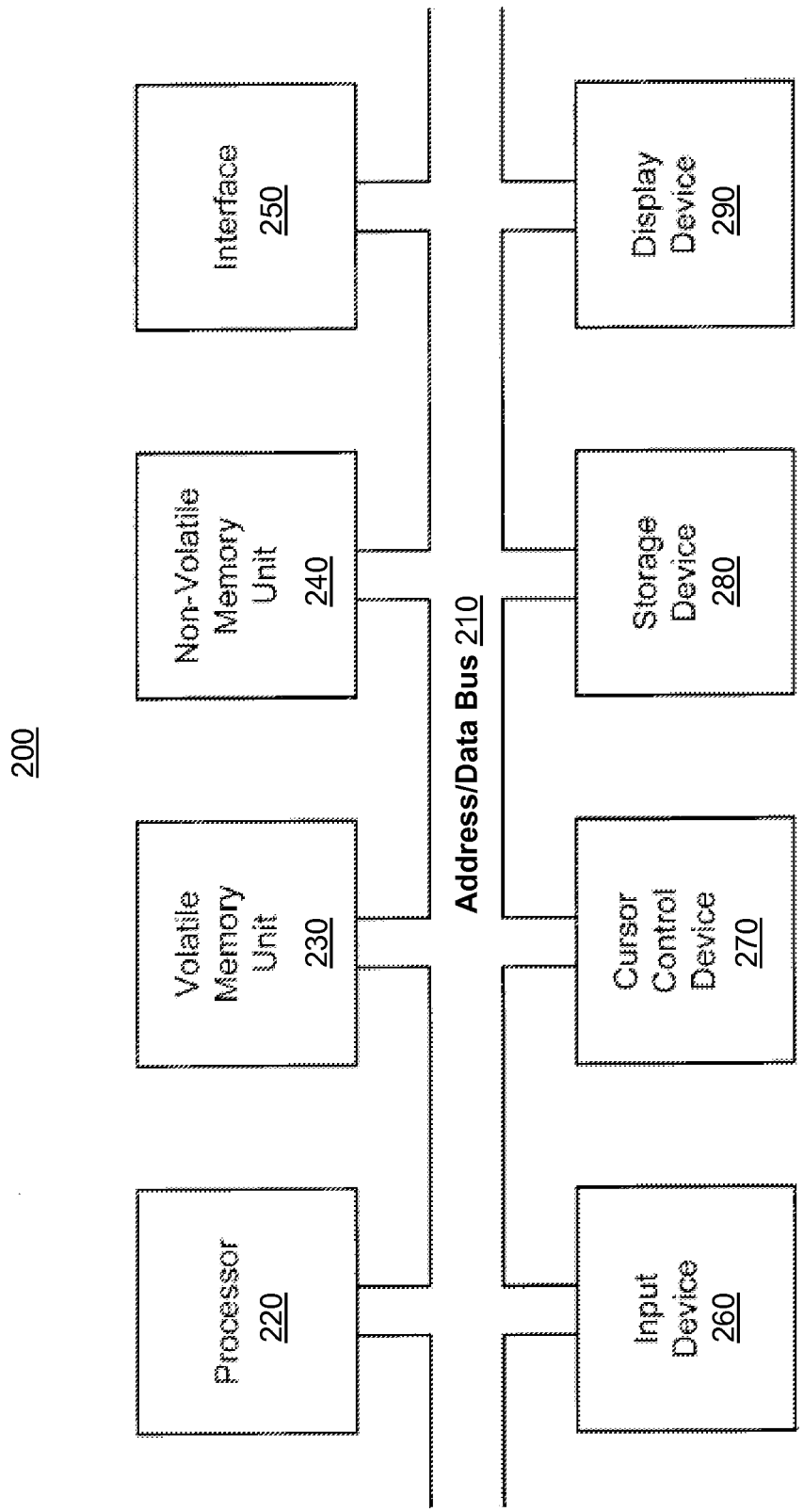
FIG. 2 shows a simplified schematic of an exemplary computer system that may be utilized in variations of the invention.

An exemplary computer system 200 in accordance with some embodiments is shown in FIG. 2. Exemplary computer system 200 is configured to perform calculations, processes, operations, and/or functions associated with a program or algorithm. In some embodiments, certain processes and steps discussed herein are realized as a series of instructions (e.g., software program) that reside within computer-readable memory units and are executed by one or more processors of exemplary computer system 200. When executed, the instructions cause exemplary computer system 200 to perform specific actions and exhibit specific behavior, such as described herein.

Exemplary computer system 200 may include an address/data bus 210 that is configured to communicate information. Additionally, one or more data processing units, such as processor 220, are coupled with address/data bus 210. Processor 220 is configured to process information and instructions. In some embodiments, processor 220 is a microprocessor. Alternatively, processor 220 may be a different type of processor such as a parallel processor, or a field-programmable gate array.

Exemplary computer system 200 is configured to utilize one or more data-storage units. Exemplary computer system 200 may include a volatile memory unit 230, such as (but not limited to) random access memory ("RAM"), static RAM, or dynamic RAM, etc.) coupled with address/data bus 210, wherein volatile memory unit 230 is configured to store information and instructions for processor 220. Exemplary computer system 200 further may include a non-volatile memory unit 240, such as (but not limited to) read-only memory ("ROM"), programmable ROM ("PROM"), erasable programmable ROM ("EPROM"), electrically erasable programmable ROM "EEPROM"), or flash memory coupled with address/data bus 210, wherein non-volatile memory unit 240 is configured to store static information and instructions for processor 220. Alternatively exemplary computer system 200 may execute instructions retrieved from an online data-storage unit such as in "cloud computing."

In some embodiments, exemplary computer system 200 also may include one or more interfaces, such as interface 250, coupled with address/data bus 210. The one or more interfaces are configured to enable exemplary computer system 200 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In some embodiments, exemplar computer system 200 may include an input device 260 coupled with address/data bus 210, wherein input device 260 is configured to communicate information and command selections to processor 220. In accordance with certain embodiments, input device 260 is an alphanumeric input device, such as a keyboard, that may include alphanumeric and/or function keys. Alternatively, input device 260 may be an input device other than an alphanumeric input device. In some embodiments, exemplar computer system 200 may include a cursor control device 270 coupled with address/data bus 210, wherein cursor control device 270 is configured to communicate user input information and/or command selections to processor 220. A cursor control device 270 may be implemented using a device such as a mouse, a track-ball, a track-pad, an optical tracking device, or a touch screen. A cursor control device 270 may alternatively, or additionally, be directed and/or activated via input from input device 260, such as in response to the use of special keys and key sequence commands associated with input device 260. Alternatively, or additionally, cursor control device 270 may be configured to be directed or guided by voice commands.

In some embodiments, exemplary computer system 200 further may include one or more optional computer-usable data-storage devices, such as storage device 280, coupled with address/data bus 210. Storage device 280 is configured to store information and/or computer-executable instructions. In some embodiments, storage device 280 is a storage device such as a magnetic or optical disk drive, including for example a hard disk drive ("HDD"), floppy diskette, compact disk read-only memory ("CD-ROM"), or digital versatile disk ("DVD"). In some embodiments, a display device 290 is coupled with address/data bus 210, wherein display device 290 is configured to display video and/or graphics. Display device 290 may include a cathode ray tube ("CRT"), liquid crystal display ("LCD"), field emission display ("FED"), plasma display or any other display device suitable for displaying video and/or graphic images and alphanumeric characters recognizable to a user.

Exemplary computer system 200 is presented herein as an exemplary computing environment in accordance with some embodiments. However, exemplary computer system 200 is not strictly limited to being a computer system. For example, exemplary computer system 200 may represent a type of data processing analysis that may be used in accordance with various embodiments described herein. Moreover, other computing systems may also be implemented. Indeed, the spirit and scope of the present technology is not limited to any single data processing environment. Thus, in some embodiments, one or more operations of various embodiments are controlled or implemented using computer-executable instructions, such as program modules, being executed by a computer. Such program modules may include routines, programs, objects, components and/or data structures that are configured to perform particular tasks or implement particular abstract data types. In addition, in some embodiments, one or more aspects are implemented by utilizing distributed computing environments, such as where tasks are performed by remote processing devices that are linked through a communications network, or such as where various program modules are located in both local and remote computer-storage media including memory-storage devices.

EXAMPLES

Example 1

Charge-discharge Profiles of a Lithium-ion Battery Cell with a Reference Electrode A cell is constructed with a $LiNi_{1/3}Co_{1/3}Mn_{1/3}O_2$ (L333)-based cathode on an Al mesh and a graphite-based anode on Cu foil. In particular, the positive electrode is composed of 84 wt % L333 (Toda Kogyo Corp, NCM-01ST), 3 wt % Super P carbon (MMM SA CARBON), 3 wt % KS6 (TIMCAL), and 10 wt % Kynar Flex 2801 (ELF ATOCHEM) and is pressed onto an Al mesh as a current collector. The negative electrode is composed of 89 wt % CGP-G8 (ConocoPhillips), 3 wt % Super P carbon (MMM SA CARBON), and 8 wt % Kynar Flex 2801 (ELF ATOCHEM) and is cast onto a copper foil. The lithium reference electrode is made from lithium metal compressed onto a copper foil. The capacities of the cathode and anode are evenly matched. The electrolyte is 1 M $LiPF_6$ in (1:1 v/v) ethylene carbonate-dimethyl carbonate solution. Electrochemical experiments are carried out using an Arbin battery tester at a C/10 rate with a cutoff voltage of 2.7 V and 4.1 V for the cell. The voltages of the cathode and the anode are recorded separately using two digital multimeters.

Figure 3:
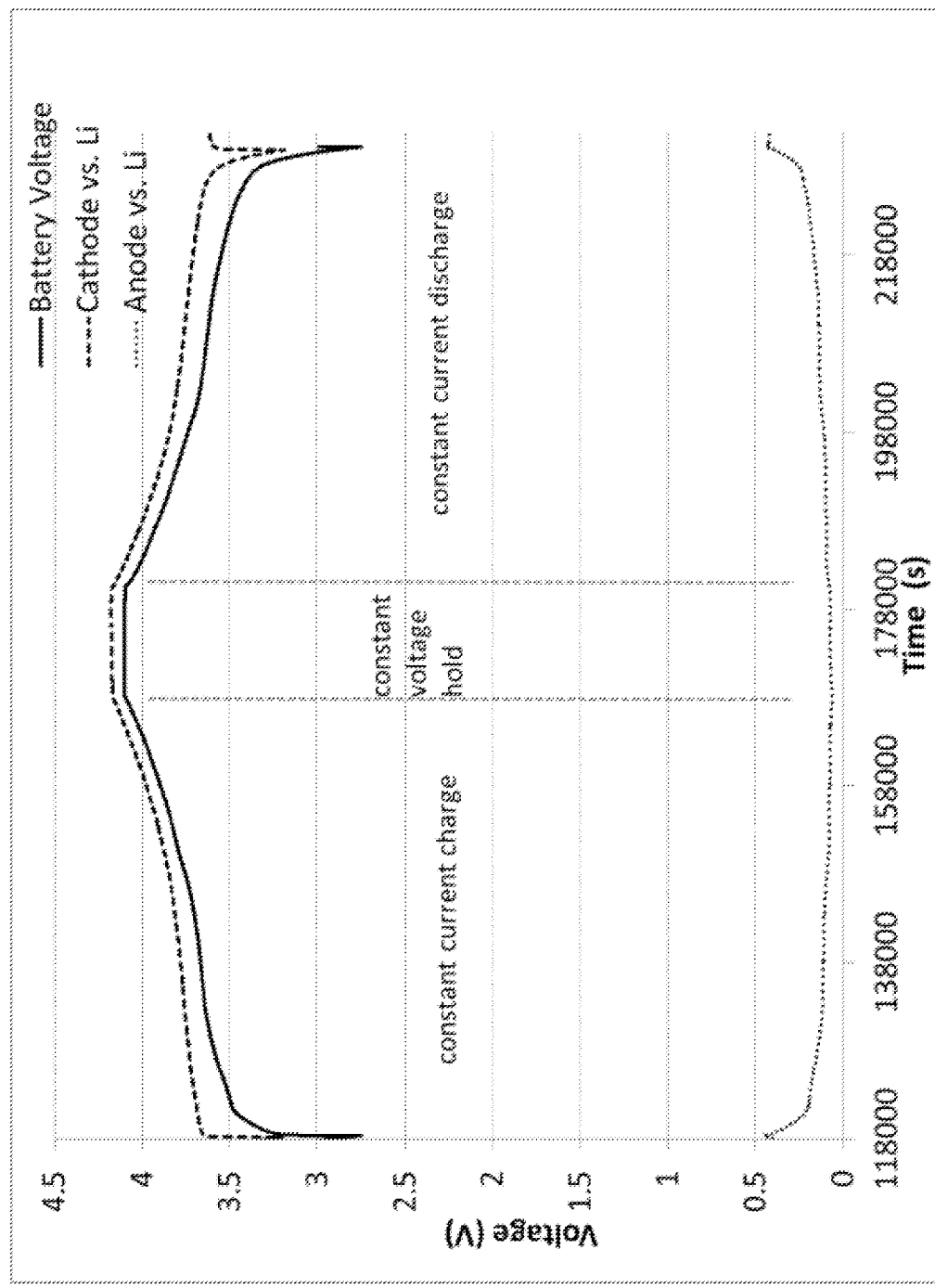
FIG. 3 plots charge-discharge profiles of a lithium-ion battery cell with reference electrode in Example 1.

FIG. 3 shows charge-discharge profiles of the lithium-ion battery cell of Example 1, where a reference electrode is used to monitor the individual cathode and anode voltage. FIG. 3 shows voltages from the full cell, the cathode, and the anode measured during a complete charge and discharge reaction using a pouch format cell with a reference electrode. The boxed numbers (1-4) in FIG. 3 refer to various scenarios that have potential safety concerns as follows:

1. During charging, the negative electrode (anode) can drop below 0 V (vs. Li), causing lithium plating and ultimately an internal short circuit.

2. During charging, the positive electrode (cathode) can over-charge beyond the safety limit, causing decomposition of the active materials and electrolytes creating an excess of heat and possible thermal runaway.

3. During discharging, the negative electrode voltage can rise above voltage safety limit, causing dissolution of metal ions from the current collector and an internal short circuit.

4. During discharging, the positive electrode voltage can drop below the voltage safety limit, causing over-discharging of positive active materials.

Without a reference electrode, only the full cell battery voltage information (solid line in FIG. 3) is available.

Example 2

Figure 4A:
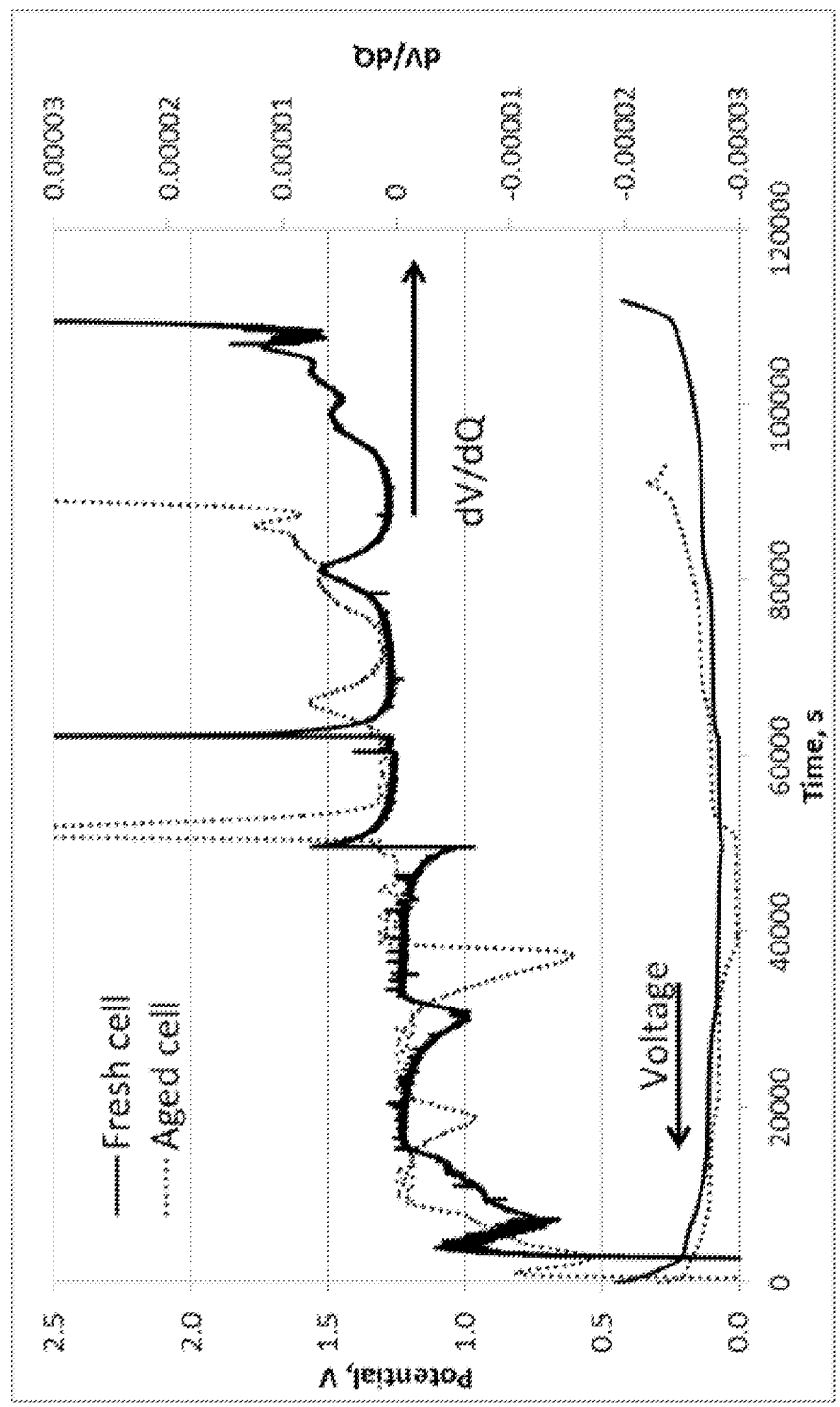
FIG. 4A depicts experimental voltage and differential voltage from a graphite-based negative electrode, in Example 2.
Figure 4B:
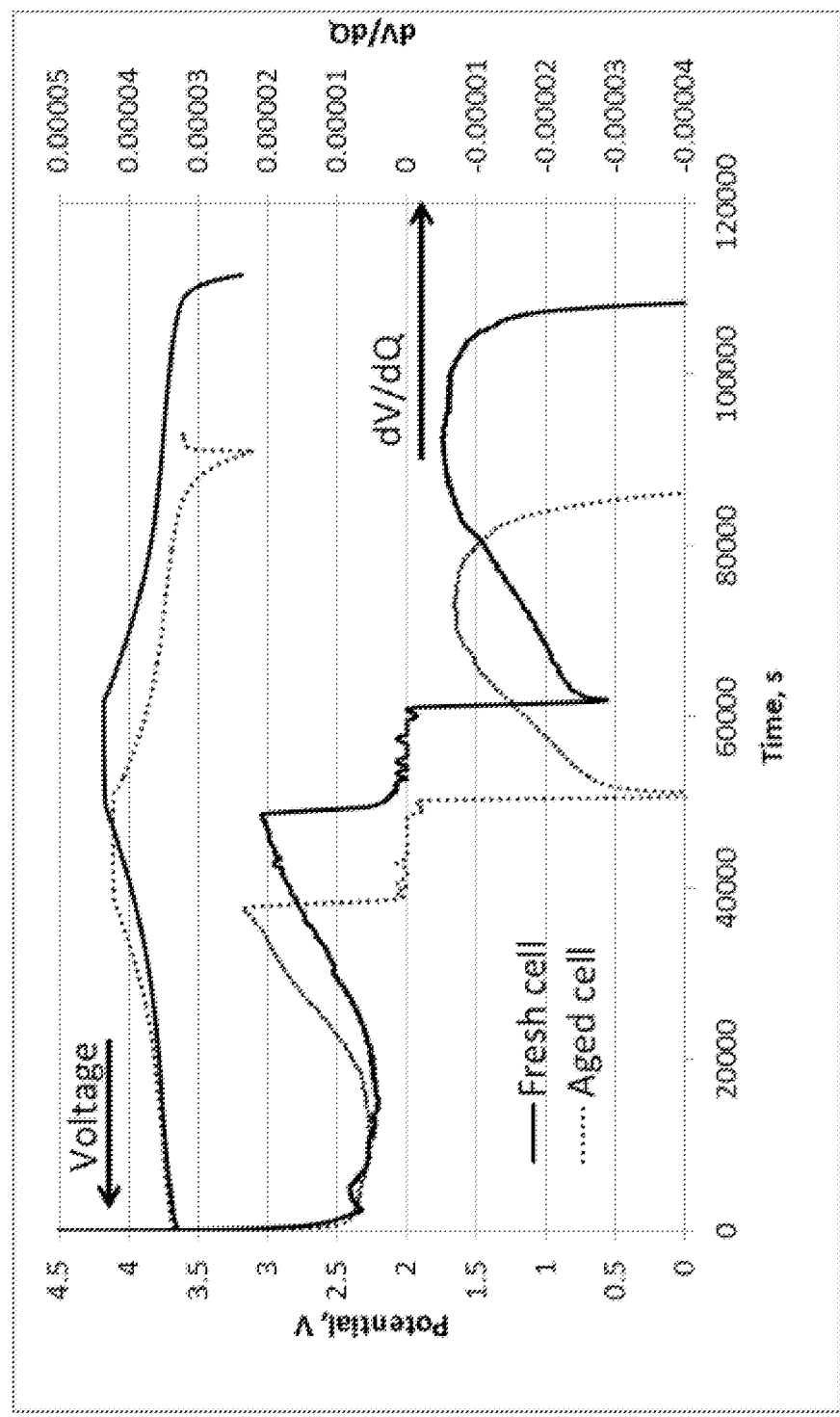
FIG. 4B depicts experimental voltage and differential voltage from a graphite-based negative electrode, in Example 2.

Use of a Reference Electrode to Monitor Voltage and Differential Voltage of Electrodes for Enhanced Battery Management, Safety, and Health Assessment FIGS. 4A and 4B depict experimental voltage and differential voltage (dV/dQ) from the graphite-based negative electrode (FIG. 4A) and the $LiNi_{1/3}Co_{1/3}Mn_{1/3}O_2$ positive electrode (FIG. 4B) before (solid lines) and after (dotted lines) cycling. The voltages are measured using a lithium reference electrode in a prismatic pouch cell design as in Example 1.

As a battery ages, the voltages of the positive and negative electrodes diverge due to resistance rise and material degradation. For example, during battery charging, the voltage of the negative electrode (FIG. 4A) is depressed to a lower voltage close to 0 V, while the positive electrode voltage (FIG. 4B) rises quickly due to the increase in resistance as the battery ages.

Example 3

Use of Positive and Negative Electrode Voltages for On-line Battery Capacity Diagnostics The voltage from individual electrodes can be used to determine each electrode's state-of-charge (SOC), during normal battery operation. These SOC values can then be used to determine electrode capacity, which tends to degrade during aging. This may be accomplished by using instances, during normal battery operation, when the current is zero (i.e., open-circuit). If this period is long enough (typically a few minutes or more), the measured voltage of each individual electrode approaches its open-circuit voltage (OCV). Using a predetermined SOC-OCV look-up table (at the appropriate temperature), we can deduce the SOC of each electrode.

The cathode capacity may be estimated according to the following derived equations. The anode equations are the same except for a change of subscripts from c (cathode) to a (anode). If two instances of open-circuit period are identified, i.e., at times $t_a$ and $t_b$, $SOC_c(t_a)$ and $SOC_c(t_b)$ can be determined. Since by definition, $$SOC_c(t_a) = \frac{Q(t_a)}{Ah_c} \quad \text{(EQ. 2)}$$

$$SOC_c(t_b) = \frac{Q(t_b)}{Ah_c} \quad \text{(EQ. 3)}$$

In EQS. 2 and 3, $Q(t_a)$ and $Q(t_b)$ are the number of coulombs available in the cathode at a time of $t_a$ and $t_b$, respectively, and $Ah_c$ is the capacity of the cathode. We also have $$Q(t_b) = Q(t_a) + \int_{t_a}^{t_b} I(t) dt \quad \text{(EQ. 4)}$$

Based on EQS. 2-4, $$Ah_c = \frac{\int_{t_a}^{t_b} I(t) dt}{SOC_c(t_b) - SOC_c(t_a)} \quad \text{(EQ. 5)}$$

Similarly, for the anode we obtain $$Ah_a = \frac{\int_{t_a}^{t_b} I(t) dt}{SOC_a(t_a) - SOC_a(t_b)} \quad \text{(EQ. 6)}$$

In the case of constant current I, then EQS. 5 and 6 can be simplified as $$Ah_c = \frac{I(t)(t_b - t_a)}{SOC_c(t_b) - SOC_c(t_a)} \quad \text{(EQ. 7)}$$

and $$Ah_a = \frac{I(t)(t_b - t_a)}{SOC_a(t_a) - SOC_a(t_b)} \quad \text{(EQ. 8)}$$

The constant-current scenario is not uncommon in vehicle batteries, such as during overnight charging. In this Example 3, this idea is tested with a Li-ion three-electrode pouch cell. The cell uses a porous current collector design that is readily implemented in commercial cells without major modifications of the battery cell design. The anode is graphite, the cathode is Li—NMC (lithium nickel manganese cobalt oxide), and the reference electrode is Li metal.

Figure 5A:
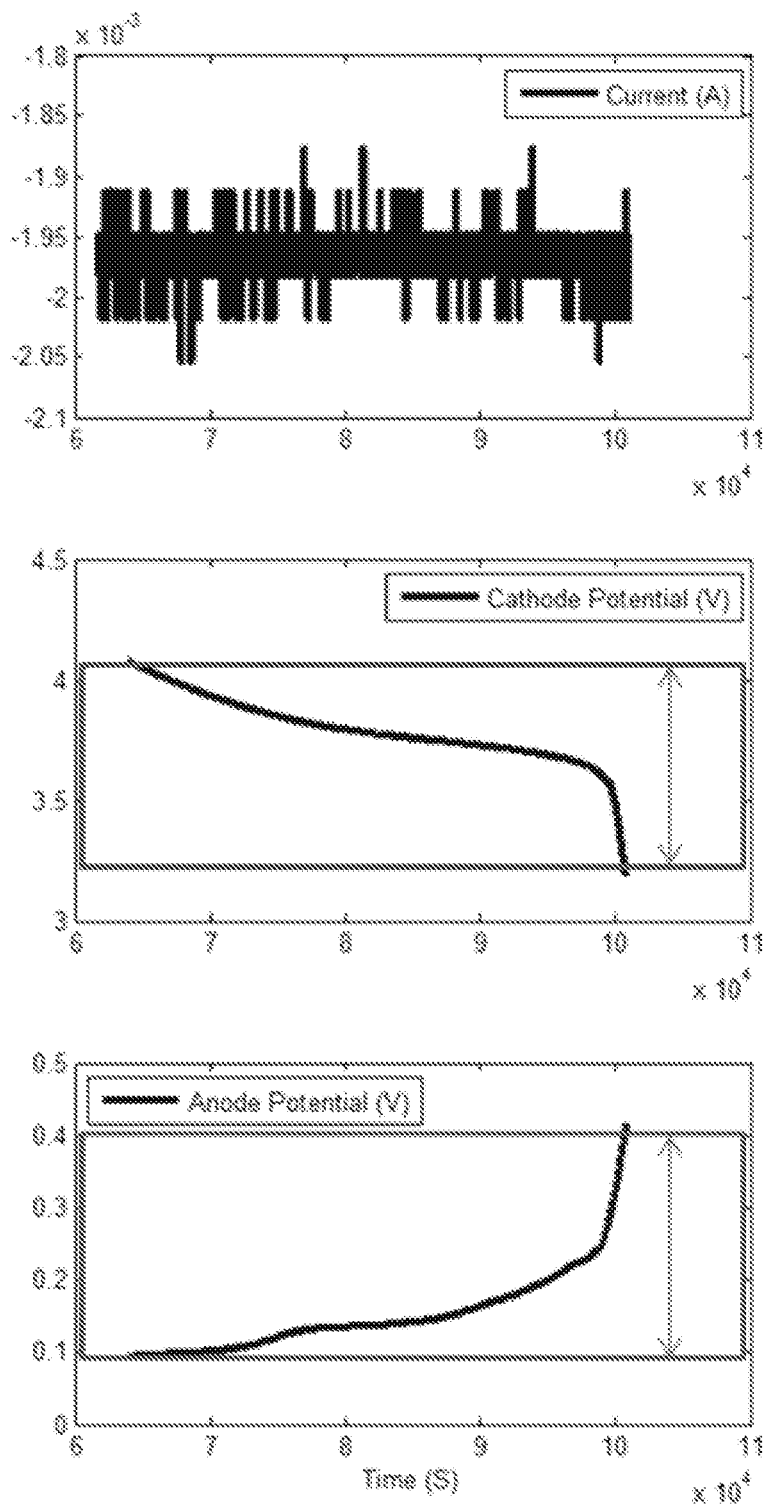
FIG. 5A shows current (top), cathode voltage (middle), and anode voltage data for Example 3.

An Arbin BT2000 is used to drive the three-electrode pouch cell and to acquire the current, anode voltage, cathode voltage, and temperature in real time. The first step is to compile a look-up table (LUT) for each electrode at room temperature. The cell is discharged from its fully charged state (about −2 mA) and the current, anode voltage, and cathode voltage are recorded (FIG. 5A). The nominal capacity of each electrode is determined by defining the voltage range of the anode and cathode ($V_{a,min}$=0.095 V, $V_{a,max}$=0.41 V; =3.15 V, $V_{c,max}$=4.05 V) and integrating the current. In this case, we obtain $Ah_{a,nominal}$=$Ah_{c,nominal}$=22.82 mAh. Finally, look-up tables are compiled for each electrode (FIG. 5B for cathode and FIG. 5C for anode) using the OCV-SOC relationship.

Figure 5B:
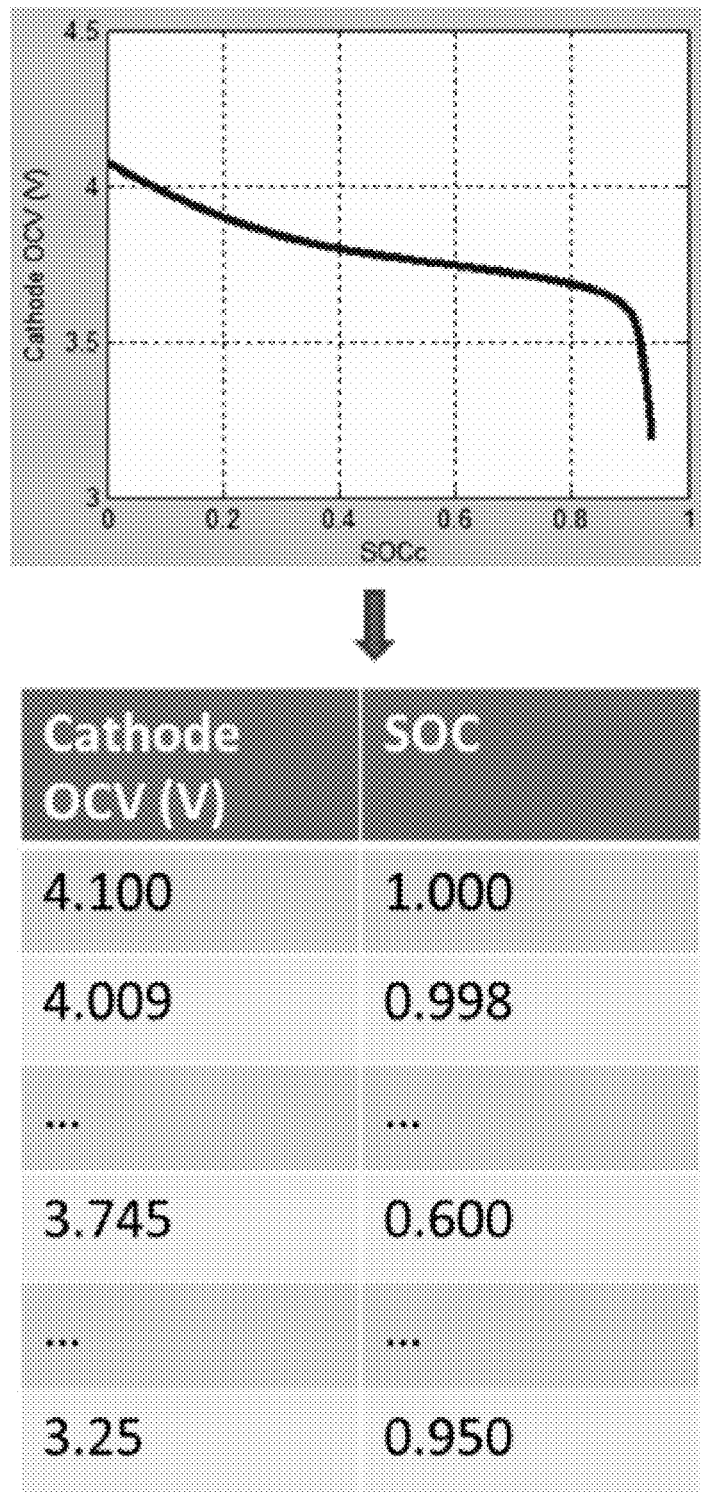
FIG. 5B illustrates how a cathode OCV-SOC look-up table may be established, in Example 3.
Figure 5C:
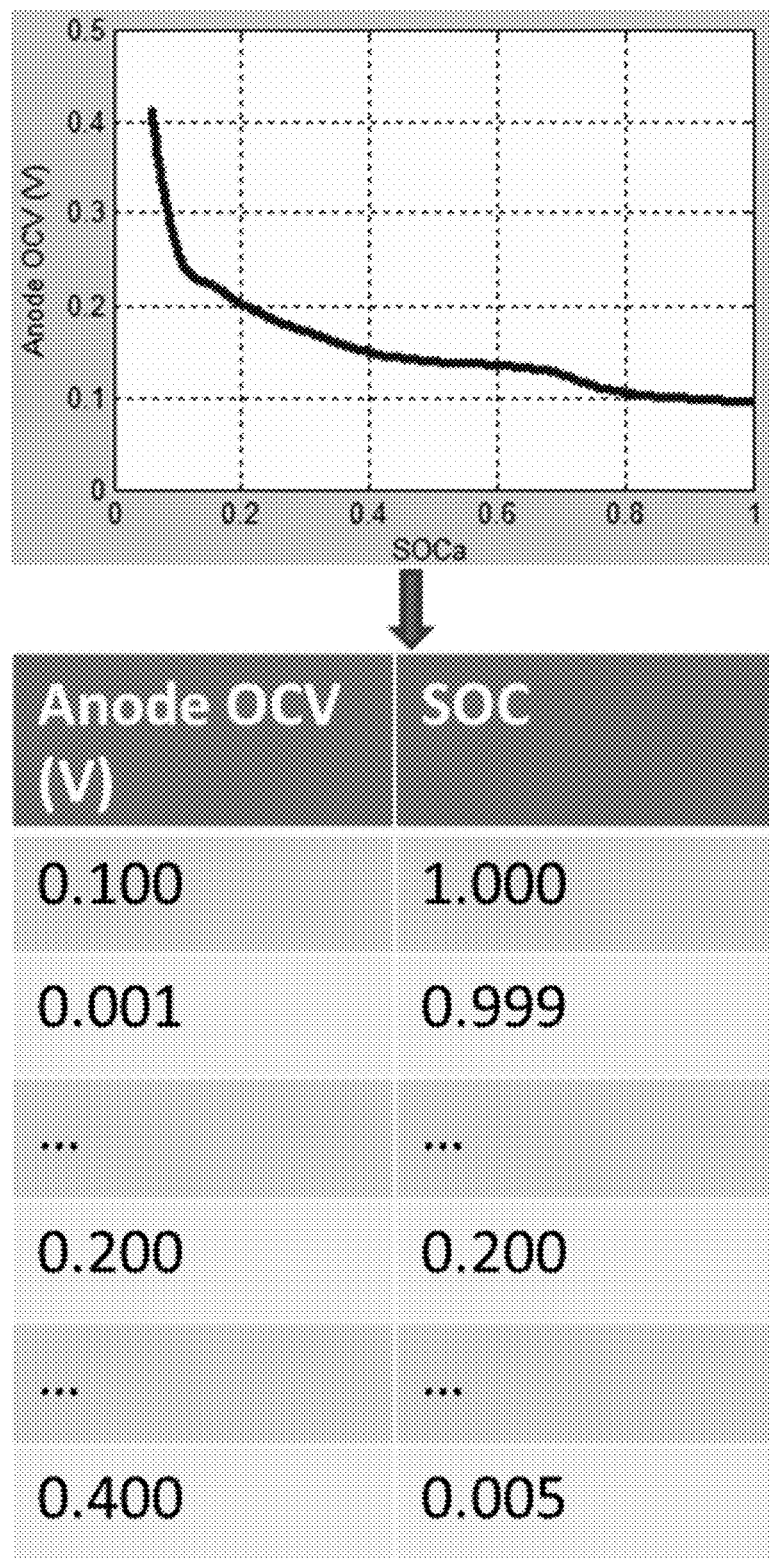
FIG. 5C illustrates how an anode OCV-SOC look-up table may be established, in Example 3.

FIGS. 5A-5C depict the method in this Example 3 by which OCV-SOC look-up tables are compiled for the cathode and the anode. In FIG. 5A, the cell is discharged and the current (top), cathode voltage (middle), and anode voltage (bottom) are recorded. These values are used to determine the cathode OCV-SOC look-up table in FIG. 5B, and the anode OCV-SOC look-up table in FIG. 5C.

Figure 6A:
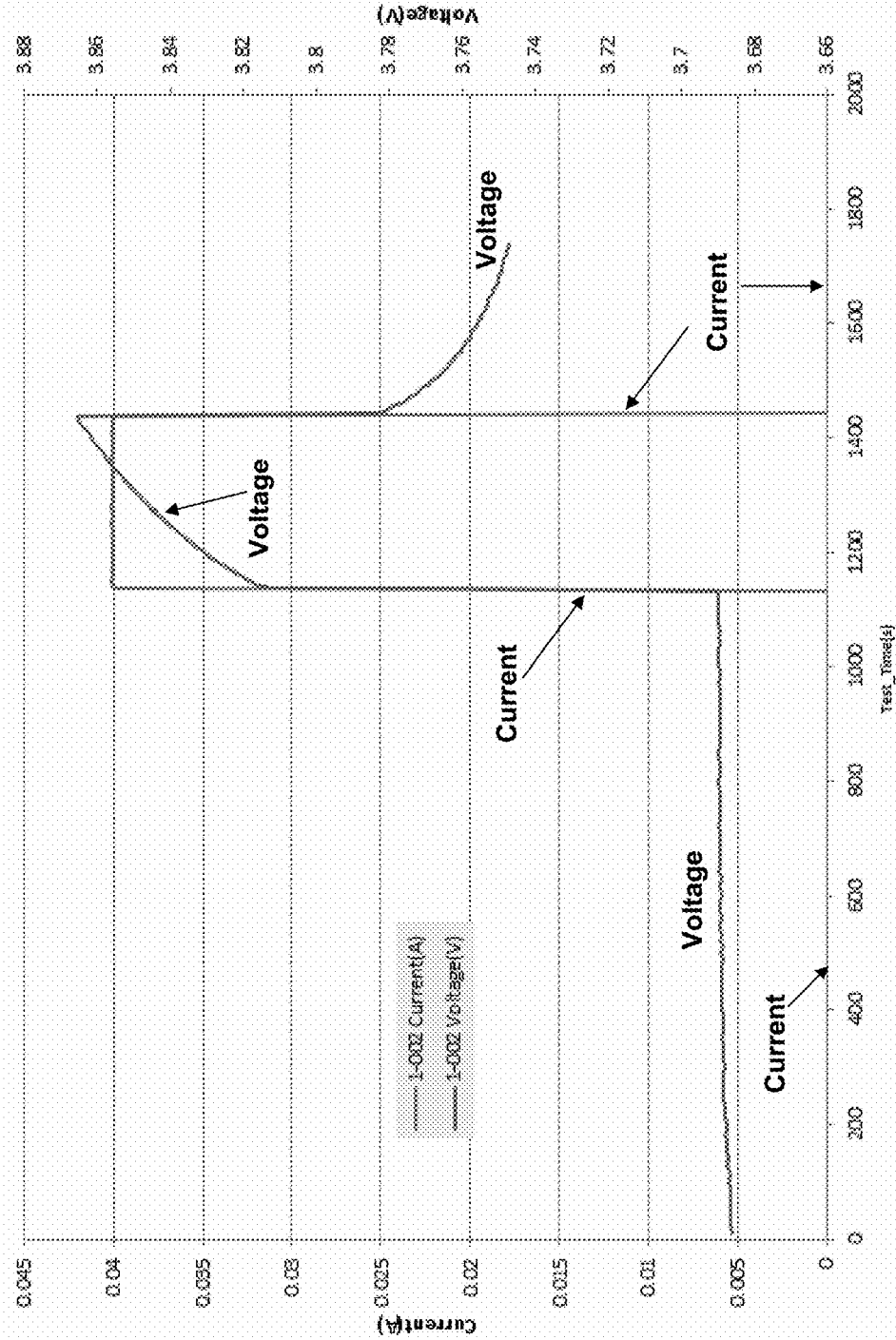
FIG. 6A plots current and voltage data during a rest period followed by a 5 min charge at 2 C rate, in Example 3.
Figure 6B:
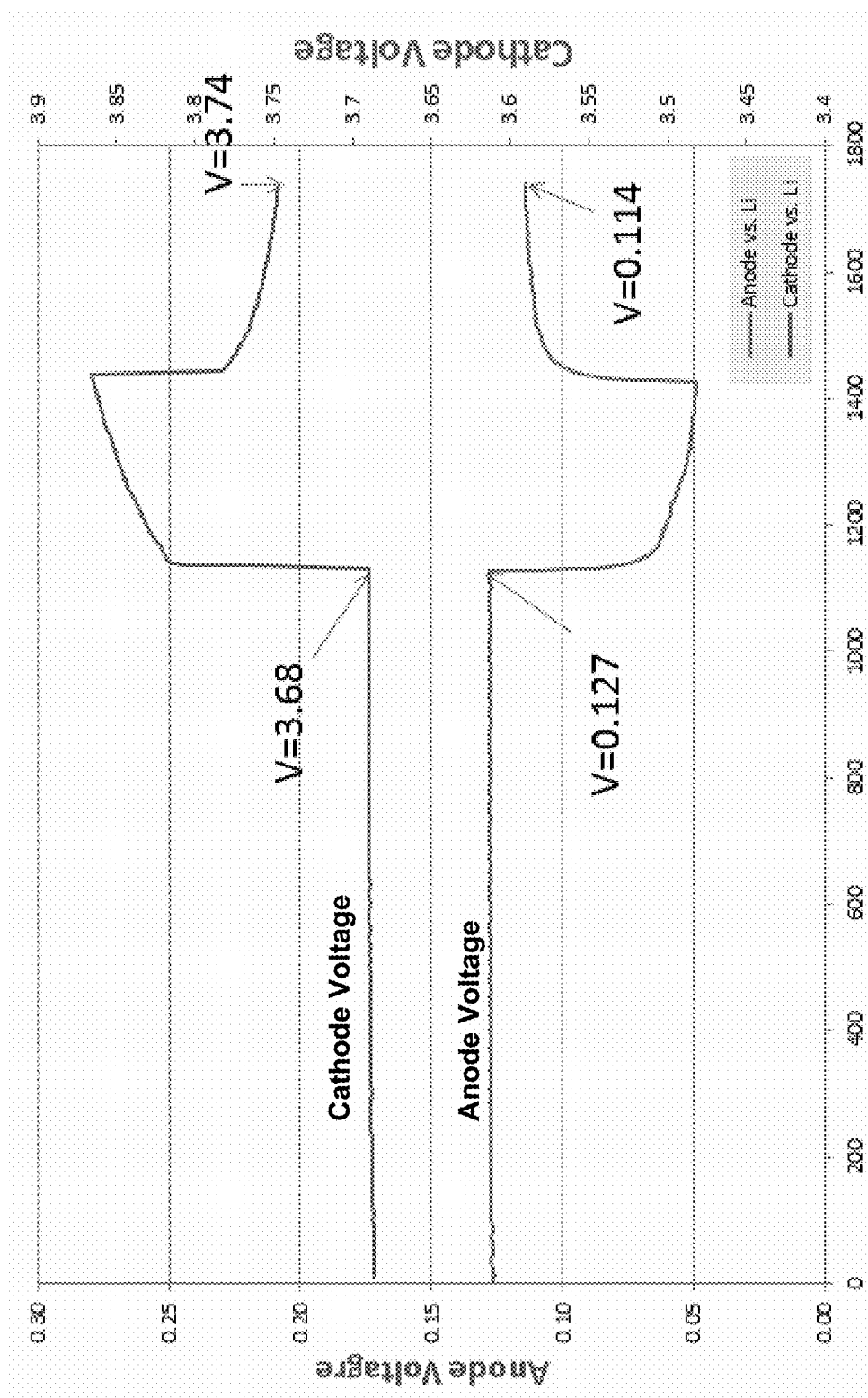
FIG. 6B plots anode and cathode voltage versus time (in seconds) and open-circuit voltages are determined at two different points (during a period of about zero current) for both the anode and the cathode, in Example 3.

The next step is to demonstrate the on-line assessment of the capacity state of health ($SOH_{Ah}$) of each electrode. The cell is driven at a 2 C rate for 5 minutes and the current and voltage are measured at room temperature, as shown in FIG. 6A. In FIG. 6A, current and voltage are recorded during a rest period followed by a 5 min charge at 2 C. Two instants are identified, $t_1$=1170 s and $t_2$=1750 s, and the measured voltages are regarded as OCVs of each electrode at these times, as shown in FIG. 6B. OCVs are determined at two different points (during a period of about zero current) for both the anode and the cathode (FIG. 6B).

For the cathode, we have $OCV_1$=3.68 V and $OCV_2$=3.74 V. Using the SOC values from the look-up table in FIG. 5B, we estimate $SOC_1$=0.76 and $SOC_2$=0.60. For the anode, we have $OCV_1$=0.127 V and $OCV_2$=0.114 V. Using the SOC values from the look-up table in FIG. 5C, we estimate $SOC_1$=0.79 and $SOC_2$=0.64.

According to EQS. 7 and 8, we then have cathode and anode capacities in real time as follows:

$$Ah_c = \frac{0.04A \times (5/60)h}{0.76 - 0.6} = 0.0208 \text{ Ah}$$

and $$Ah_a = \frac{0.04A \times (5/60)h}{0.79 - 0.64} = 0.022 \text{ Ah}$$

Example 4

Figure 7:
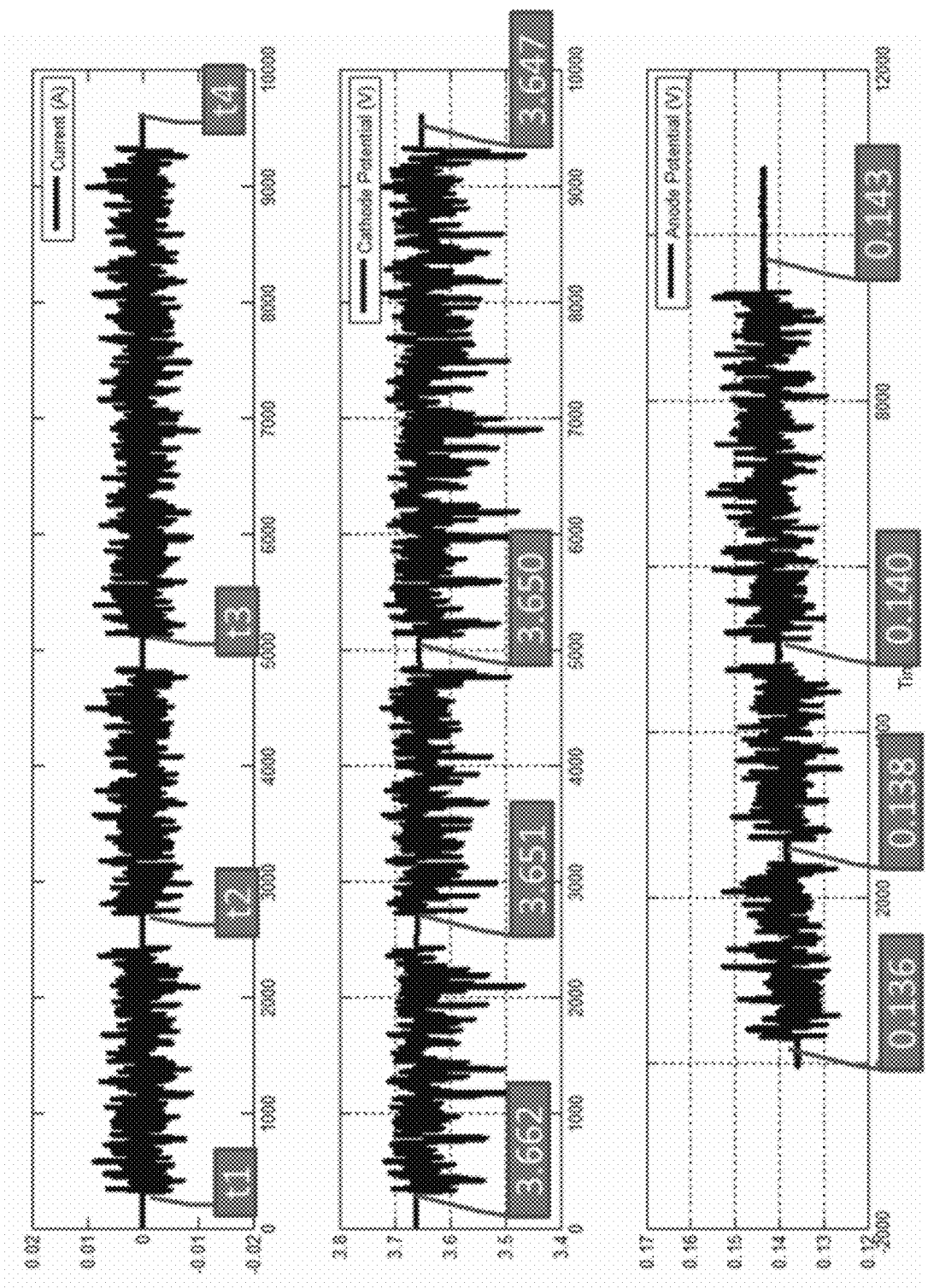
FIG. 7 shows experiments data obtained from a three-electrode pouch cell driven with a random profile, displaying current (top graph), cathode voltage (middle graph), and anode voltage (bottom graph) according to Example 4.

Use of Positive and Negative Electrode Voltages for On-line Battery Capacity Diagnostics This Example 4 utilizes the methodology and equations derived above in Example 3. FIG. 7 shows experiments data obtained from a three-electrode pouch cell driven with a random profile. FIG. 7 shows current (top graph), cathode voltage (middle graph), and anode voltage (bottom graph). The times selected ($t_1$, $t_2$, $t_3$, and $t_4$) correspond to the end of a rest period (zero current) and are used to determine OCV and SOC of each electrode. These values, determined at two (or more) times selected from $t_1$, $t_2$, $t_3$, and $t_4$, are then used to calculate the capacity of each electrode.

In this particular scenario, we drive the cell (same cell as in Example 3) with a random cycling profile, and identify four instants ($t_1$, $t_2$, $t_3$, and $t_4$—top graph of FIG. 7) that can be used for sampling the OCVs, as shown in FIG. 7. We choose two instants for demonstration, $t_1$ and $t_4$. With $V_{cathode,1}=3.662$ V and $V_{cathode,4}=3.647$ V, the cathode SOCs are determined using the look-up table in FIG. 5B, whereby it is estimated that $\Delta SOC_{cathode}=0.064$. Similarly, with $V_{anode,1}=0.136$ V and $V_{anode,4}=0.143$ V, the anode SOCs are determined using the look-up table in FIG. 5C, whereby it is estimated that $\Delta SOC_{anode}=0.071$. The current is integrated over time using a digital trapezoidal method from $t_1$ to $t_4$, resulting in 1.54 mAh coulombs.

From these values and EQS. 7 and 8, the cathode capacity is calculated as $Ah_c=1.54$ mAh/$0.064=0.024$ Ah and the anode capacity is calculated as $Ah_a=1.54$ mAh/$0.071=0.0217$ Ah. These are anode and cathode capacities in real time for the battery.

There are a wide variety of practical and commercial uses for the present invention. Applications of the algorithms in diagnosing battery systems include, but are not limited to, battery diagnostics for in-flight batteries on satellites, aircraft, or other aviation vehicles; real-time management of traction batteries for electric vehicles or hybrid-electric vehicles; and battery-pack management for soldier power and ground vehicles.

This invention will benefit commercial applications where battery safety, battery health, and battery life information are important. Especially for automobiles and airplanes, knowledge of battery health/life information as well as battery safety is critical to meet customer satisfaction. Direct measurements of the battery electrode potentials can greatly improve the battery safety and enhance the accuracy and reliability of battery management.

The current invention may also impact other commercial military and space applications such as consumer portable electronics, electric bikes, power tools, aircrafts, and satellites that can benefit from better health/life monitoring at a reduced costs. Practical applications for this invention include, but are not limited to, laptop computers, mobile phones, cameras, medical devices, electric vehicles, electric bikes, scooters, and power tools.

In this detailed description, reference has been made to multiple embodiments and to the accompanying drawings in which are shown by way of illustration specific exemplary embodiments of the invention. These embodiments are described to enable those skilled in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

All publications, patents, and patent applications cited in this specification are herein incorporated by reference in their entirety as if each publication, patent, or patent application were specifically and individually put forth herein.

The embodiments, variations, and figures described above should provide an indication of the utility and versatility of the present invention. Other embodiments that do not provide all of the features and advantages set forth herein may also be utilized, without departing from the spirit and scope of the present invention. Such modifications and variations are considered to be within the scope of the invention defined by the claims.

What is claimed is:

1. An apparatus for real-time monitoring of anode and cathode voltage, anode and cathode differential voltage, and anode and cathode state of charge in a metal-ion battery, wherein said apparatus is linked in operable communication with said battery, said apparatus comprising:
a first voltage monitor that is connectable between said anode and a reference electrode of said battery; a second voltage monitor that is connectable between said cathode and said reference electrode, wherein a porous current collector is interposed between said reference electrode, on the one hand, and both of said anode and said cathode, on the other hand, to allow communication of metal ions (i) away from a metal-ion path between said cathode said anode and (ii) toward said reference electrode; and a computer programmed using non-transitory memory with executable code for executing the steps of:
receiving anode voltage signals derived from said first voltage monitor at a plurality of times;
receiving cathode voltage signals derived from said second voltage monitor at said plurality of times;
receiving or calculating a derivative of the anode voltage with respect to time and/or a derivative of the anode voltage with respect to capacity at said plurality of times;
receiving or calculating a derivative of the cathode voltage with respect to time and/or a derivative of the cathode voltage with respect to capacity at said plurality of times;
receiving current signals derived from battery current at said plurality of times;
identifying a first time and a second time, within said plurality of times, such that said battery current is 0 A for at least 1 minute, wherein between said first time and said second time, there exists an intermediate time such that said battery current is greater than 0 A;
estimating first and second anode open-circuit voltages from said anode voltage signals at said first and second times, respectively;
correlating said first and second anode open-circuit voltages to first and second anode states of charge at said first and second times, respectively;
estimating first and second cathode open-circuit voltages from said cathode voltage signals at said first and second times, respectively; and
correlating said first and second cathode open-circuit voltages to first and second cathode states of charge at said first and second times, respectively.

2. The apparatus of claim 1, wherein said computer is programmed to execute the step of estimating one or more battery states selected from the group consisting of state of power, state of health, state of safety, and combinations thereof.

3. The apparatus of claim 1, wherein said computer is further programmed to execute the step of estimating anode capacity or anode remaining capacity based on said first and second anode states of charge.

4. The apparatus of claim 1, wherein said computer is further programmed to execute the step of estimating cathode capacity or cathode remaining capacity based on said first and second cathode states of charge.

5. The apparatus of claim 1, wherein said battery is a lithium-ion battery.

6. An apparatus for real-time assessment of capacity of both anode and cathode in a metal-ion battery, wherein said apparatus is linked in operable communication with said battery, said apparatus comprising:
 a first voltage monitor that is connectable between said anode and a reference electrode of said battery; a second voltage monitor that is connectable between said cathode and said reference electrode, wherein a porous current collector is interposed between said reference electrode, on the one hand, and both of said anode and said cathode, on the other hand, to allow communication of metal ions (i) away from a metal-ion path between said cathode said anode and (ii) toward said reference electrode; and a computer programmed using non-transitory memory with executable code for executing the steps of:
 receiving anode voltage signals derived from said first voltage monitor at a plurality of times;
 receiving cathode voltage signals derived from said second voltage monitor at said plurality of times;
 receiving current signals derived from battery current at said plurality of times;
 estimating, at a first time and a second time within said plurality of times, first and second anode open-circuit voltages and correlating said first and second anode open-circuit voltages to first and second anode states of charge, respectively;
 calculating anode capacity as the integral of said current signals from said first time to said second time, divided by the difference between said second and first anode states of charge;
 estimating, at said first time and said second time, first and second cathode open-circuit voltages and correlating said first and second cathode open-circuit voltages to first and second cathode states of charge, respectively; and
 calculating cathode capacity as the integral of said current signals from said first time to said second time, divided by the difference between said second and first cathode states of charge,
 wherein said first and second times are selected such that said battery current is 0 A for at least 1 minute, wherein between said first time and said second time, there exists an intermediate time such that said battery current is greater than 0 A,
 wherein said first and second anode open-circuit voltages are each estimated as anode voltage at said first and second times, respectively, and
 wherein said first and second cathode open-circuit voltages are each estimated as cathode voltage at said first and second times, respectively.

7. The apparatus of claim 6, wherein said first and second times are selected such that said battery current is about 0 for at least 2 minutes.

8. The apparatus of claim 6, wherein said first and second times are selected such that said battery current is about 0 for at least 5 minutes.

9. The apparatus of claim 6, wherein said first and second anode open-circuit voltages are correlated to said first and second anode states of charge using a look-up table, graph, equation, or combination thereof.

10. The apparatus of claim 6, wherein said first and second cathode open-circuit voltages are correlated to said first and second cathode states of charge using a look-up table, graph, equation, or combination thereof.

11. The apparatus of claim 6, wherein said battery is a lithium-ion battery.

12. A method of real-time monitoring of anode and cathode voltage, anode and cathode differential voltage, and anode and cathode state of charge in a metal-ion battery, said method comprising:
 providing a first voltage monitor connected between said anode and a reference electrode of said battery;
 providing a second voltage monitor connected between said cathode and said reference electrode, wherein a porous current collector is interposed between said reference electrode, on the one hand, and both of said anode and said cathode, on the other hand, to allow communication of metal ions (i) away from a metal-ion path between said cathode said anode and (ii) toward said reference electrode;
 providing a computer in operable communication with said battery;
 receiving, in said computer, anode voltage signals derived from said first voltage monitor at a plurality of times;
 receiving, in said computer, cathode voltage signals derived from said second voltage monitor at said plurality of times;
 receiving or calculating, in said computer, a derivative of the anode voltage with respect to time and/or a derivative of the anode voltage with respect to capacity at said plurality of times;
 receiving or calculating, in said computer, a derivative of the cathode voltage with respect to time and/or a derivative of the cathode voltage with respect to capacity at said plurality of times;
 receiving current signals derived from battery current at said plurality of times;
 identifying a first time and a second time, within said plurality of times, such that said battery current is 0 A for at least 1 minute, wherein between said first time and said second time, there exists an intermediate time such that said battery current is greater than 0 A;
 estimating first and second anode open-circuit voltages from said anode voltage signals at said first and second times, respectively;
 correlating said first and second anode open-circuit voltages to first and second anode states of charge at said first and second times, respectively;
 estimating first and second cathode open-circuit voltages from said cathode voltage signals at said first and second times, respectively; and
 correlating said first and second cathode open-circuit voltages to first and second cathode states of charge at said first and second times, respectively.

13. The method of claim 12, said method further comprising estimating, in said computer, one or more battery states selected from the group consisting of state of power, state of health, state of safety, and combinations thereof.

14. The method of claim 12, wherein said method further comprises estimating, in said computer, anode capacity or anode remaining capacity based on said first and second anode states of charge.

15. The method of claim 12, wherein said method further comprises estimating, in said computer, cathode capacity or cathode remaining capacity based on said first and second cathode states of charge.

16. The method of claim 12, wherein said anode voltage signals and/or said cathode voltage signals are compared, in said computer, to predetermined voltage safety limits of said anode and/or said cathode, respectively.

17. The method of claim 12, wherein said derivative of said anode or cathode voltage with respect to time and/or said derivative of said anode or cathode voltage with respect to capacity is compared, in said computer, to predetermined differential voltage safety limits of said anode and/or said cathode, respectively.

18. A method of real-time assessment of capacity of both anode and cathode in a metal-ion battery, said method comprising:
providing a first voltage monitor connected between said anode and a reference electrode of said battery;
providing a second voltage monitor connected between said cathode and said reference electrode, wherein a porous current collector is interposed between said reference electrode, on the one hand, and both of said anode and said cathode, on the other hand, to allow communication of metal ions (i) away from a metal-ion path between said cathode said anode and (ii) toward said reference electrode;
providing a computer in operable communication with said battery;
operating said battery with a driving profile;
receiving, in said computer, anode voltage signals derived from said first voltage monitor at a plurality of times;
receiving, in said computer, cathode voltage signals derived from said second voltage monitor at said plurality of times;
receiving, in said computer, current signals derived from battery current at said plurality of times;
estimating, in said computer, at a first time and a second time within said plurality of times, first and second anode open-circuit voltages and correlating, in said computer, said first and second anode open-circuit voltages to first and second anode states of charge, respectively;
calculating, in said computer, anode capacity as the integral of said current signals from said first time to said second time, divided by the difference between second and first anode states of charge;
estimating, in said computer, at said first time and said second time, first and second cathode open-circuit voltages and correlating, in said computer, said first and second cathode open-circuit voltages to first and second cathode states of charge, respectively; and
calculating, in said computer, cathode capacity as the integral of said current signals from said first time to said second time, divided by the difference between said second and first cathode states of charge,
wherein said first and second times are selected such that said battery current is 0 A for at least 1 minute, wherein between said first time and said second time, there exists an intermediate time such that said battery current is greater than 0 A,
wherein said first and second anode open-circuit voltages are each estimated, in said computer, as anode voltage measured at said first and second times, respectively, and
wherein said first and second cathode open-circuit voltages are each estimated, in said computer, as cathode voltage measured at said first and second times, respectively.

19. The method of claim 18, wherein said first and second times are selected such that said battery current is about 0 for at least 2 minutes.

20. The method of claim 19, wherein said battery current is about 0 for at least 5 minutes prior to recording each of said first and second measured anode voltage as each of said first and second anode open-circuit voltages, respectively.

21. The method of claim 19, wherein said battery current is about 0 for at least 5 minutes prior to recording each of said first and second measured cathode voltage as each of said first and second cathode open-circuit voltages, respectively.

22. The method of claim 18, wherein said anode capacity is determined as constant-discharge current multiplied by the time period for discharging anode voltage from its minimum to maximum.

23. The method of claim 18, wherein said cathode capacity is determined as constant-discharge current multiplied by the time period for discharging cathode voltage from its minimum to maximum.

24. The method of claim 18, wherein said first and second anode open-circuit voltages are correlated, in said computer, to said first and second anode states of charge using a look-up table, graph, equation, or combination thereof.

25. The method of claim 18, wherein said first and second cathode open-circuit voltages are correlated, in said computer, to said first and second cathode states of charge using a look-up table, graph, equation, or combination thereof.

26. The method of claim 18, said method further comprising receiving, in said computer, battery temperature signals at said plurality of times; and wherein said first and second anode open-circuit voltages are correlated, in said computer, to said first and second anode states of charge using a look-up table, graph, equation, or combination thereof which accounts for variation of anode state of charge with temperature.

27. The method of claim 18, said method further comprising receiving, in said computer, battery temperature signals at said plurality of times; and wherein said first and second cathode open-circuit voltages are correlated, in said computer, to said first and second cathode states of charge using a look-up table, graph, equation, or combination thereof which accounts for variation of anode state of charge with temperature.

* * * * *